(12) United States Patent
June et al.

(10) Patent No.: US 10,577,407 B2
(45) Date of Patent: Mar. 3, 2020

(54) USE OF ICOS-BASED CARS TO ENHANCE ANTITUMOR ACTIVITY AND CAR PERSISTENCE

(71) Applicant: The Trustees of the University of Pennsylvania, Philadelphia, PA (US)

(72) Inventors: Carl H. June, Merion Station, PA (US); Sonia Guedan Carrio, Philadelphia, PA (US); Yangbing Zhao, Cherry Hill, NJ (US); John Scholler, Narberth, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/637,734

(22) Filed: Jun. 29, 2017

(65) Prior Publication Data
US 2017/0362295 A1    Dec. 21, 2017

Related U.S. Application Data

(62) Division of application No. 14/376,038, filed as application No. PCT/US2013/027366 on Feb. 22, 2013, now Pat. No. 9,714,278.

(60) Provisional application No. 61/601,910, filed on Feb. 22, 2012.

(51) Int. Cl.
| | |
|---|---|
| *A01N 63/00* | (2006.01) |
| *A61K 48/00* | (2006.01) |
| *C07K 14/705* | (2006.01) |
| *C07K 14/725* | (2006.01) |
| *A61K 35/12* | (2015.01) |

(52) U.S. Cl.
CPC ............ *C07K 14/705* (2013.01); *A61K 35/12* (2013.01); *C07K 14/7051* (2013.01); *C07K 14/70503* (2013.01); *C07K 14/70517* (2013.01); *C07K 14/70521* (2013.01); *C07K 2319/03* (2013.01)

(58) Field of Classification Search
CPC .................................................... C07K 14/705
USPC ..................................................... 424/93.21
See application file for complete search history.

(56) References Cited

U.S. PATENT DOCUMENTS

| | | |
|---|---|---|
| 5,190,878 A | 3/1993 | Wilhelm et al. |
| 5,199,942 A | 4/1993 | Gillis et al. |
| 5,350,674 A | 9/1994 | Boenisch et al. |
| 5,585,362 A | 12/1996 | Wilson et al. |
| 5,858,358 A | 1/1999 | June et al. |
| 5,883,223 A | 3/1999 | Gray |
| 5,888,807 A | 3/1999 | Palsson et al. |
| 5,985,653 A | 11/1999 | Armstrong et al. |
| 5,993,434 A | 11/1999 | Dev et al. |
| 6,096,532 A | 8/2000 | Armstrong et al. |
| 6,120,766 A | 9/2000 | Hale et al. |
| 6,181,964 B1 | 1/2001 | Hofmann et al. |
| 6,233,482 B1 | 5/2001 | Hofmann et al. |
| 6,241,701 B1 | 6/2001 | Hofmann et al. |
| 6,326,193 B1 | 12/2001 | Liu et al. |
| 6,352,694 B1 | 3/2002 | June et al. |
| 6,516,223 B2 | 2/2003 | Hofmann et al. |
| 6,534,055 B1 | 3/2003 | June et al. |
| 6,678,556 B1 | 1/2004 | Nolan et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,171,264 B1 | 1/2007 | Hofmann et al. |
| 7,172,869 B2 | 2/2007 | June et al. |
| 7,173,116 B2 | 2/2007 | Fewell et al. |
| 7,175,843 B2 | 2/2007 | June et al. |
| 7,232,566 B2 | 6/2007 | June et al. |
| 7,368,110 B2 | 5/2008 | Pastan et al. |
| 2004/0014645 A1 | 1/2004 | Draghia-Akli et al. |
| 2004/0043401 A1 | 3/2004 | Sadelain et al. |
| 2004/0059285 A1 | 3/2004 | Mathiesen et al. |
| 2004/0092907 A1 | 5/2004 | Mathiesen et al. |
| 2004/0101519 A1 | 5/2004 | June et al. |
| 2005/0052630 A1 | 3/2005 | Smith et al. |
| 2005/0070841 A1 | 3/2005 | Mathiesen et al. |
| 2005/0113564 A1 | 5/2005 | Campana et al. |
| 2006/0034810 A1 | 2/2006 | Riley et al. |
| 2006/0247191 A1 | 11/2006 | Finney et al. |
| 2007/0128708 A1 | 6/2007 | Gamelin et al. |

FOREIGN PATENT DOCUMENTS

| | | |
|---|---|---|
| WO | 0129058 A1 | 4/2001 |
| WO | 2004039840 A1 | 5/2004 |
| WO | 2005044996 A2 | 5/2005 |
| WO | 2010025177 A1 | 3/2010 |

OTHER PUBLICATIONS

European Patent Application No. 13751777.7—Communication pursuant to Article 94(3) EPC dated Jan. 18, 2018.
Chinese Patent Application No. 201380010754.9—First Office Action dated Mar. 16, 2016.
Eurasian Region Patent Application No. 201491574/28—Office Action dated May 4, 2016.
European Patent Application No. 13751777.7—European Search Report dated Nov. 24, 2015.
Genbank BC025703.1 (http://www.ncbi.nlm.nih.gov/nuccore/BC025703.1 . . . Jul. 15, 2006) accessed on Apr. 26, 2016.

(Continued)

*Primary Examiner* — Valarie E Bertoglio
(74) *Attorney, Agent, or Firm* — Saul Ewing Arnstein & Lehr LLP; Kathryn Doyle

(57) ABSTRACT

The present invention provides compositions and methods for treating cancer in a human. The invention includes administering a genetically modified Th17 cell to express a CAR having an antigen binding domain, a transmembrane domain, and an ICOS intracellular signaling domain.

15 Claims, 13 Drawing Sheets

Specification includes a Sequence Listing.

(56) References Cited

OTHER PUBLICATIONS

International Search Report for PCT/US2013/027366 dated May 3, 2013.
Singapore Patent Application No. 11201404769U—Search Report of the Intellectual Property Office of Singapore dated Jun. 10, 2015.
Singapore Patent Application No. 11201404769U—Written Opinion dated Mar. 29, 2016.
Singapore Patent Application No. 11201404769U—Written Opinion of Intellectual Property Office of Singapore dated Aug. 28, 2015.
Bauquet, et al., "The costimulatory molecule ICOS regulates the expression of c-Maf and IL-21 in the development of follicular T helper cells and TH-17 cells", 2009 Nat. Immunol. 10:167-175.
Berry, et al., "Adoptive immunotherapy for cancer: the next generation of gene-engineered immune cells.", Tissue Antigens. Oct. 2009;74(4):277-89.
Bierer, et al., "Cyclosporin A and FK506: molecular mechanisms of immunosuppression and probes for transplantation biology", Curr. Opin. Immun. 5:763-773, 1993.
Bird, et al., "Single-chain antigen-binding proteins", 1988, Science 242:423-426.
Carpenito, et al., "Control of large, established tumor xenografts with genetically retargeted human T cells containing CD28 and CD137 domains.", 2009, PNAS 106(9):3360-3365.
Cougot, et al., "'Cap-tabolism'", Trends in Biochem. Sci., 29:436-444 (2001) (Abstract).
Elango, et al., "Optimized transfection of mRNA transcribed from a d(A/T)100 tail-containing vector", Biochim. Biophys. Res. Commun., 330:958-966 (2005) (Abstract).
Finney, et al., "Activation of resting human primary T cells with chimeric receptors: costimulation from CD28, inducible costimulator, CD134, and CD137 in series with signals from the TCR zeta chain", 2004, J Immunol 172:104-113.
Guedan, et al., "ICOS-based chimeric antigen receptors program bipolar TH17/TH1 cells", 2014, Blood 124 (7):1070-1080.
Guedan, "Redirection of TH17 cells with an ICOS-based CAR enhances function, antitumor activity and persistence of TH17 cells", 2012, Human Gene Therapy 23(10):A34-A35.
Henderson, et al., "Comparison of the effects of FK-506, cyclosporin A and rapamycin on IL-2 production", Immun. 73:316-321, 1991.
Huston, et al., "Protein engineering of antibody binding sites: recovery of specific activity in an anti-digoxin single-chain Fv analogue produced in *Escherichia coli*.", 1988, Proc. Natl. Acad. Sci. USA 85:5879-5883.
Hutloff, et al., "ICOS is an inducible T-cell co-stimulator structurally and functionally related to CD28.", Nature. Jan. 21, 1999;397(6716):263-6.

Jena, et al., "Redirecting T-cell specificity by introducing a tumor-specific chimeric antigen receptor", 2010, Blood 116:1035-1044.
Korn, et al., "IL-17 and Th17 Cells", 2009 Annu. Rev. Immunol. 27:485-517.
Liu, et al., "Calcineurin Is a Common Target of Cyclophilin-Cyclosporin A and FKBP-FK506 Complexes", Cell 66:807-815, 1991.
Mumtaz, et al., "Design of liposomes for circumventing the reticuloendothelial cells", 1991 Glycobiology 5: 505-10.
Murphy, et al., "Effector T cell plasticity: flexibility in the face of changing circumstances", 2010 Nat. Immunol. 11:674-680.
Nacheva, et al., "Preventing nondesired RNA-primed RNA extension catalyzed by T7 RNA polymerase", Eur. J. Biochem., 270:1485-65 (2003).
Nishikawa, et al., "Nonviral vectors in the new millennium: delivery barriers in gene transfer.", Hum Gene Ther., 12 (8):861-70 (2001) (Abstract).
O'Shea, et al., "Mechanisms underlying lineage commitment and plasticity of helper CD4+T cells", 2010 Science 327:1098-1102.
Park, et al., "A distinct lineage of CD4 T cells regulates tissue inflammation by producing interleukin 17", 2005 Nat. Immunol. 6:1133-1141.
Paulos, et al., The Inducible Costimulator (ICOS) Is Critical for the Development of Human TH17 Cells. 2010, Science Translational Medicine 2(55):55ra78.
Rosenberg, et al., "Use of Tumor-Infiltrating Lymphocytes and Interleukin-2 in the Immunotherapy of Patients with Metastatic Melanoma", New Eng. J. of Med. 319:1676-1680, 1988.
Schenborn, et al., "A novel transcription property of SP6 and T7 RNA polymerases: dependence on template structure", Nuc Acids Res., 13:6223-36 (1985).
Shen, et al., "Chimeric antigen receptor containing ICOS signaling domain mediates specific and efficient antitumor effect of T cells against EGFRvIII expressing glioma", 2013, Journal of Hematology and Oncology 6(1):33.
Stepinski, "Synthesis and properties of mRNAs containing the novel "anti-reverse" cap analogs 7-methyl(3'-O-methyl)GpppG and 7-methyl(3'-deoxy)GpppG", RNA, 7:1468-95 (2001).
Ui-Tei, et al., "Sensitive assay of RNA interference in *Drosophila* and Chinese hamster cultured cells using firefly luciferase gene as target", 2000 FEBS Letters 479: 79-82.
Zou, et al., "TH17 cells in tumour immunity and immunotherapy." 2010 Nat. Rev. Immunol. 10:248-256.
European Patent Application No. 13751777.7—Office Action dated Oct. 17, 2018.
Canadian Patent Application No. 2,864,688—Office Action dated Feb. 12, 2019.

```
atggccttac cagtgaccgc cttgctcctg ccgctggcct tgctgctcca cgccgccagg
ccgggatccc aggtacaact gcagcagtct gggcctgagc tggagaagcc tggcgcttca
gtgaagatat cctgcaaggc ttctggttac tcattcactg gctacaccat gaactgggtg
aagcagagcc atggaaagag ccttgagtgg attggactta ttactcctta caatggtgct
tctagctaca accagaagtt cagggcaag gccacattaa ctgtagacaa gtcatccagc
acagcctaca tggacctcct cagtctgaca tctgaagact ctgcagtcta tttctgtgca
agggggggtt acgacgggag gggttttgac tactggggcc aagggaccac ggtcaccgtc
tcctcaggtg gaggcggttc aggcggcggt ggctctagcg gtggcggatc ggacatcgag
ctcactcagt ctccagcaat catgtctgca tctccagggg agaaggtcac catgacctgc
agtgccagct caagtgtaag ttacatgcac tggtaccagc agaagtcagg cacctccccc
aaaagatgga tttatgacac atccaaactg gcttctggag tcccaggtcg cttcagtggc
agtgggtctg gaaactctta ctctctcaca atcagcagcg tggaggctga agatgatgca
acttattact gccagcagtg gagtaagcac cctctcacgt acggtgctgg gacaaagttg
gaaatcaaag ctagcaccac gacgccagcg ccgcgaccac caacaccggc gcccaccatc
gcgtcgcagc ccctgtccct gcgcccagag gcgtgccggc cagcggcggg gggcgcagtg
cacacgaggg ggctggactt cgcctgtgat ttcgaattct ggttacccat aggatgtgca
gcctttgttg tagtctgcat tttgggatgc atacttattt gttggcttac aaaaaagaag
tattcatcca gtgtgcacga ccctaacggt gaatacatgt tcatgagagc agtgaacaca
gccaaaaaat ccagactcac agatgtgacc ctaactagta gagtgaagtt cagcaggagc
gcagacgccc ccgcgtacaa gcaggccag aaccagctct ataacgagct caatctagga
cgaagagagg agtacgatgt tttggacaag agacgtggcc gggaccctga gatgggggga
aagccgagaa ggaagaaccc tcaggaaggc ctgtacaatg aactgcagaa agataagatg
gcggaggcct acagtgagat tgggatgaaa ggcgagcgcc ggaggggcaa ggggcacgat
ggcctttacc agggtctcag tacagccacc aaggacacct acgacgccct tcacatgcag
gccctgcccc ctcgc
```

SEQ ID NO: 8

Figure 1

Figure 2A
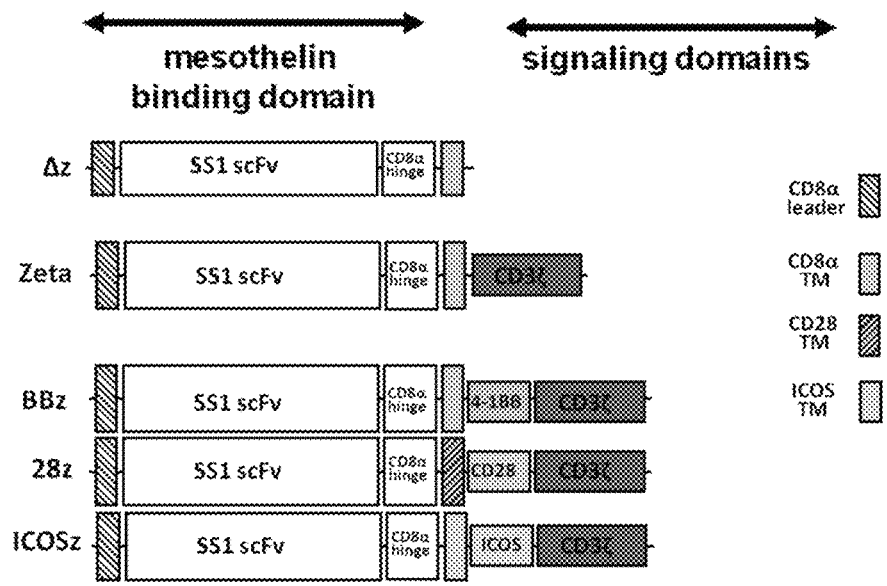
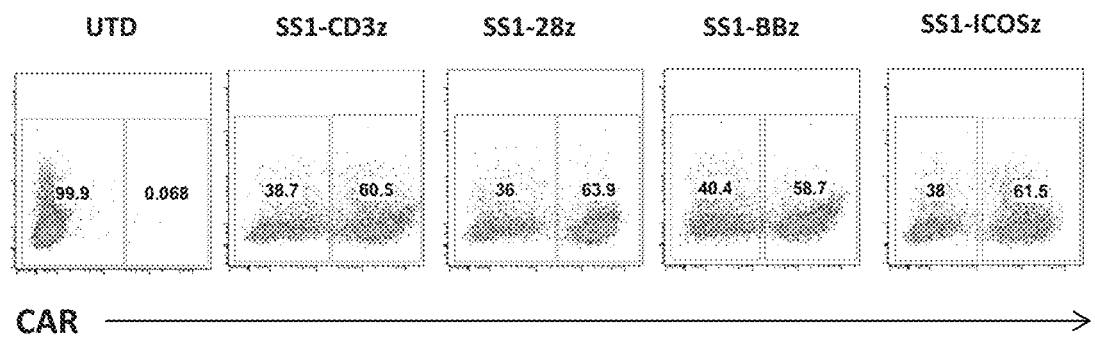
Figure 2B

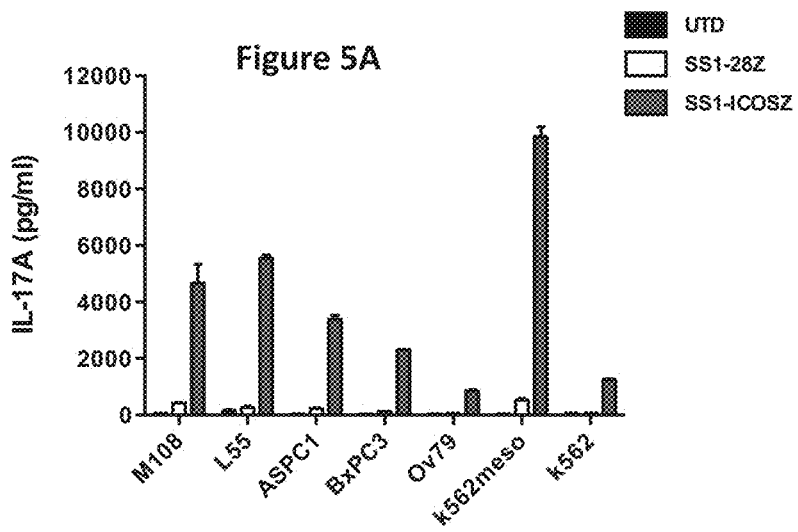
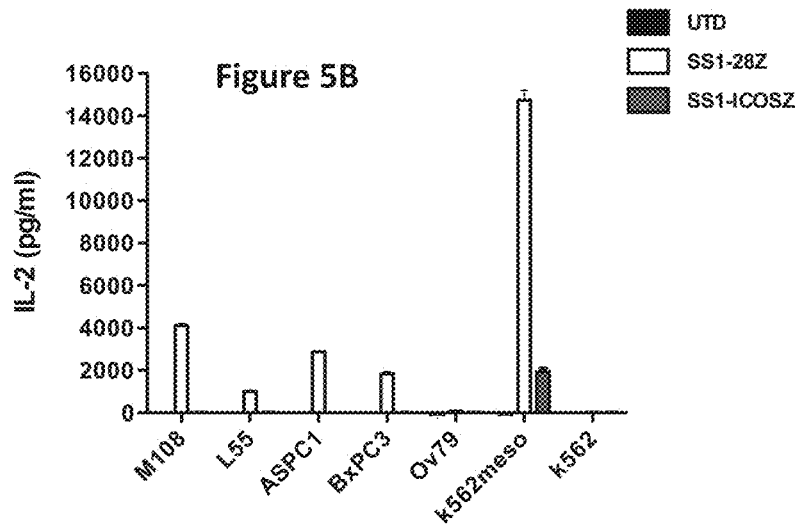
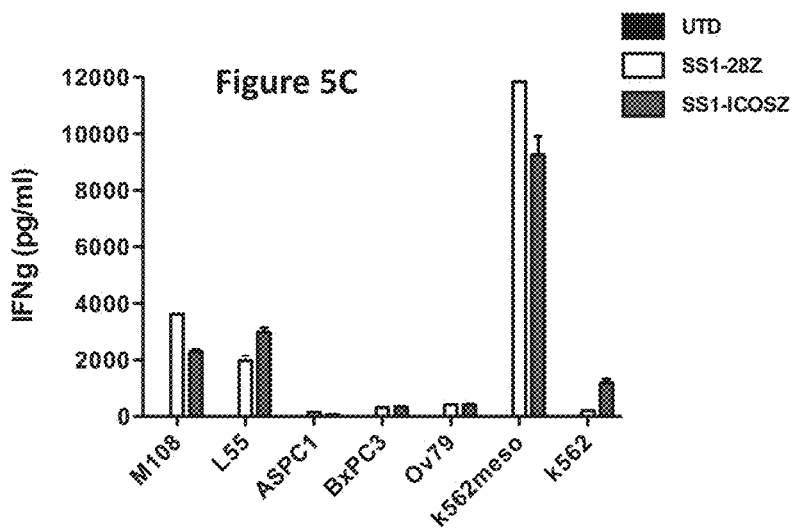

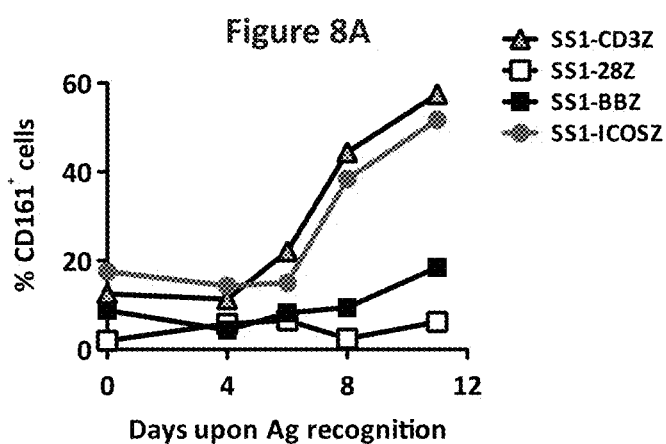
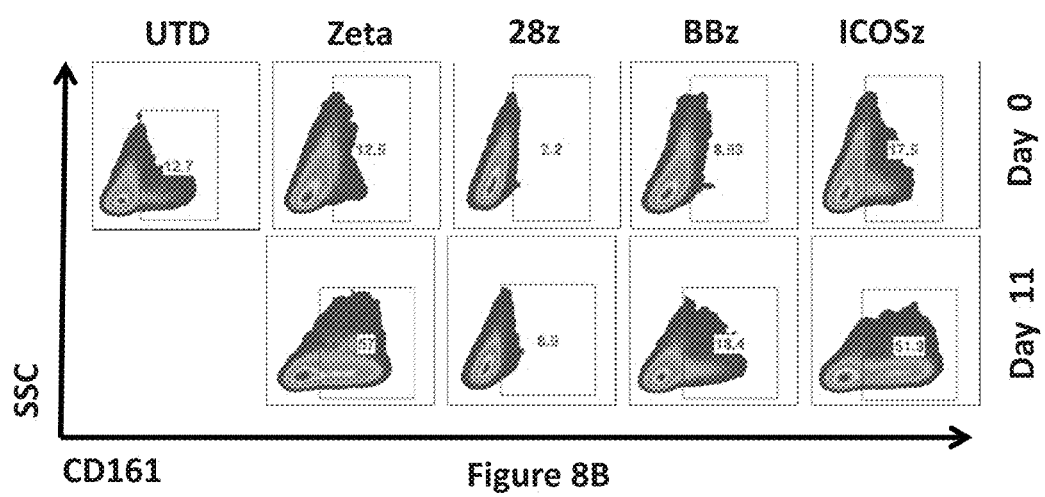

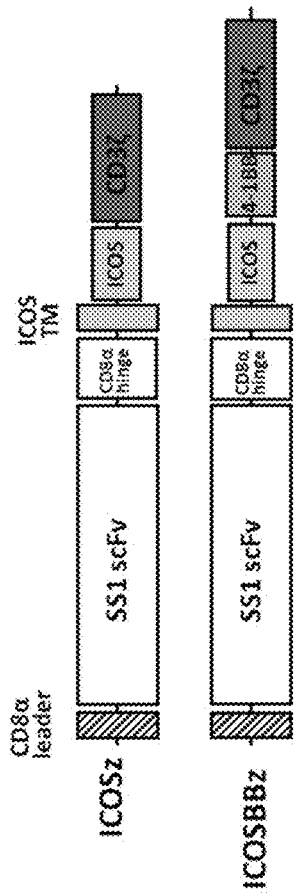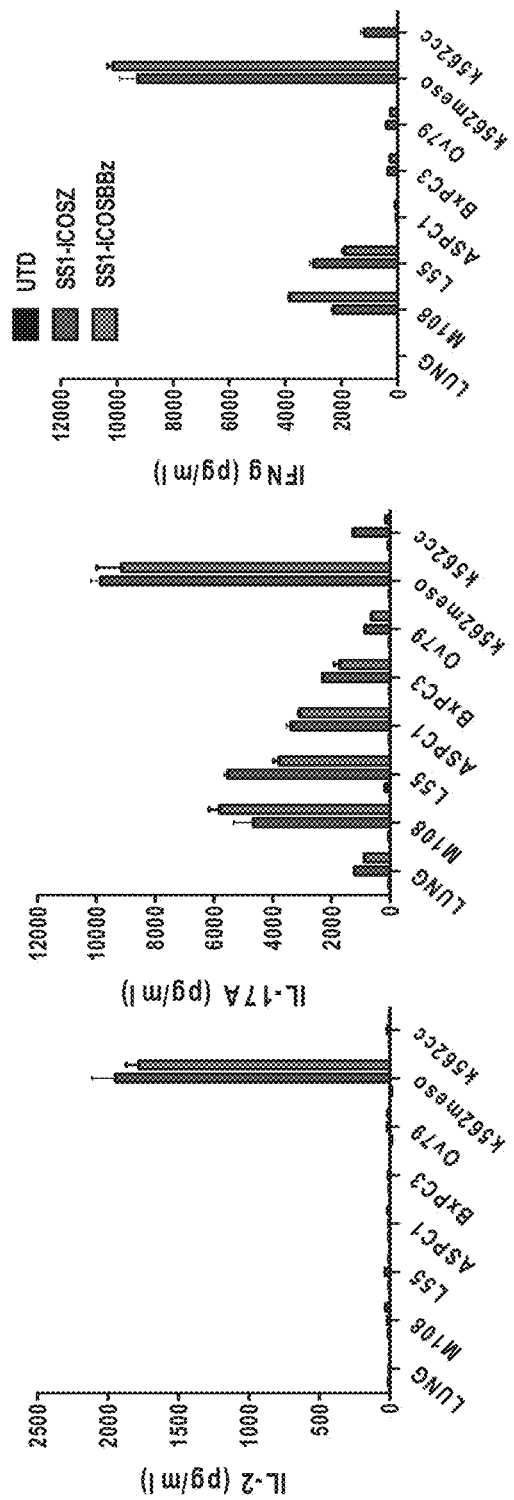
Figure 9A
Figure 9B

USE OF ICOS-BASED CARS TO ENHANCE ANTITUMOR ACTIVITY AND CAR PERSISTENCE

CROSS-REFERENCE TO RELATED APPLICATION

This application is a divisional of U.S. patent application Ser. No. 14/376,038, filed Jul. 31, 2014, now U.S. Pat. No. 9,714,278, which is a U.S. national phase application filed under 35 U.S.C. § 371 claiming benefit to International Patent Application No. PCT/US2013/027366 filed on Feb. 22, 2013, which is entitled to priority under 35 U.S.C. § 119(e) to U.S. Provisional Application No. 61/601,910, filed Feb. 22, 2012, each of which is hereby incorporated by reference in its entirety.

BACKGROUND OF THE INVENTION

The development of T cells which are genetically modified to express a chimeric antigen receptor (CAR) has opened the door for many new potential therapies for cancers and other disorders. Generally, CARs comprise an extracellular antigen recognition domain and an intracellular domain. The exact composition of the intracellular domain can provide unique characteristics to the CAR and to the cell population expressing the CAR.

CD278 or Inducible-T-cell costimulator (ICOS) is a costimulatory molecule that is generally expressed on activated T cells. It has been shown that in addition to CD28, signaling via the inducible costimulator (ICOS, also called CD278) is required for optimal cytokine secretion, because both molecules are essential for optimal IL-17A secretion by murine Th17 cells (Park et al., 2005 Nat. Immunol. 6:1133-1141). Recent findings in murine models have revealed that ICOS amplifies Th17 responses by inducing the expression of the transcription factor c-MAF and therefore transactivating IL-21 production (Bauquet et al., 2009 Nat. Immunol. 10:167-175). While chimeric receptors that comprise ICOS have been generated (U.S. Patent Publication US2006/0247191), it is unknown what role the ICOS domain has in influencing CAR mediated anti-tumor activity, CAR mediated Treg proliferation, or T cell persistence.

Depending on the microenvironmental cues present, naïve CD4+ T cells may differentiate into one of several T helper (TH) cell lineages, including TH1, TH2, Th17, TH22, and regulatory T (Treg) cells (O'Shea et al., 2010 Science 327:1098-1102; Murphy et al., 2010 Nat. Immunol. 11:674-680). Th17 cells augment host defense, have a major role in mucosal immunity, enhance a number of autoimmune diseases, and release cytokines, including IL-17A and IL-17F (Korn et al., 2009 Annu. Rev. Immunol. 27:485-517). The contribution of Th17 cells to tumor immunity varies, showing the potential for both antitumorigenic and protumorigenic activity (Zou et al., 2010 Nat. Rev. Immunol. 10:248-256). Therefore, identification of the mechanisms that control Th17 responses is essential to understand tumor immunity. Despite recent advances in CAR-based therapies for treating cancers, there has yet to be any known therapy using genetically redirected Th17 cells.

Thus, there is an urgent need in the art for compositions and methods for treatment of cancer using CARs that increase the anti-tumor activity and persistence of genetically redirected Th17 cells. The present invention addresses this need.

SUMMARY OF THE INVENTION

The invention provides an isolated nucleic acid sequence encoding a chimeric antigen receptor (CAR), wherein the CAR comprises an antigen binding domain, a transmembrane domain, and an ICOS intracellular signaling domain.

In one embodiment, the nucleic acid sequence of the CAR further comprises a CD3zeta signaling domain.

In one embodiment, the isolated nucleic acid sequence of the CAR comprises the nucleic acid sequence of SEQ ID NO: 8.

In one embodiment, the antigen binding domain is an antibody or an antigen-binding fragment thereof.

In one embodiment, the antigen-binding fragment is a Fab or a scFv.

In one embodiment, the antigen binding domain binds to a tumor antigen. In one embodiment, the tumor antigen is associated with a hematologic malignancy. In one embodiment, the tumor antigen is associated with a solid tumor.

In one embodiment, the tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, and any combination thereof.

In one embodiment, the nucleic acid sequence of the CAR further comprises a costimulatory signaling region comprising the intracellular domain of a costimulatory molecule selected from the group consisting of CD27, CD28, 4-1BB, OX40, CD30, CD40, PD-1, lymphocyte function-associated antigen-1 (LFA-1), CD2, CD7, LIGHT, NKG2C, B7-H3, a ligand that specifically binds with CD83, and any combination thereof.

In one embodiment, the ICOS intracellular signaling domain is encoded by the nucleic acid sequence of SEQ ID NO: 6.

In one embodiment, the CD3 zeta signaling domain is encoded by the nucleic acid sequence of SEQ ID NO: 7.

The invention also provides a vector comprising a nucleic acid sequence encoding a chimeric antigen receptor (CAR), wherein the CAR comprises an antigen binding domain, a transmembrane domain, and an ICOS intracellular signaling domain.

The invention also provides a cell comprising a nucleic acid sequence encoding a chimeric antigen receptor (CAR), wherein the CAR comprises an antigen binding domain, a transmembrane domain, and an ICOS intracellular signaling domain.

The invention also provides a method for stimulating a T cell-mediated immune response to a target cell population or tissue in a mammal, the method comprising administering to a mammal an effective amount of a cell genetically modified to express a CAR, wherein the CAR comprises an antigen binding domain, a transmembrane domain, and an ICOS intracellular signaling domain.

The invention also provides a method of providing an anti-tumor immunity in a mammal, the method comprising administering to the mammal an effective amount of a cell genetically modified to express a CAR, wherein the CAR comprises an antigen binding domain, a transmembrane domain, and an ICOS intracellular signaling domain, thereby providing an anti-tumor immunity in the mammal.

The invention also provides a method of treating a mammal having a disease, disorder or condition associated with an elevated expression of a tumor antigen, the method comprising administering to the mammal an effective amount of a cell genetically modified to express a CAR, wherein the CAR comprises an antigen binding domain, a transmembrane domain, and an ICOS intracellular signaling domain, thereby treating the mammal.

In one embodiment, the cell is selected from the group consisting of an autologous Th17 cell and an autologous Tc17 cell.

The invention also provides a method of treating a human with cancer, the method comprising administering to the human a cell genetically engineered to express a CAR, wherein the CAR comprises an antigen binding domain, a transmembrane domain, and an ICOS intracellular signaling domain, wherein the cell is selected from the group consisting of a Th17 cell and a Tc17 cell.

In one embodiment, the human is resistant to at least one chemotherapeutic agent.

The invention also provides a method of generating a persisting population of genetically engineered T cells in a human diagnosed with cancer, the method comprising administering to the human a cell genetically engineered to express a CAR, wherein the CAR comprises an antigen binding domain, a transmembrane domain, and an ICOS intracellular signaling domain, wherein the persisting population of genetically engineered cells persists in the human for at least one month after administration, and wherein the cell is selected from the group consisting of a Th17 cell and a Tc17 cell.

In one embodiment, the persisting population of genetically engineered T cells comprises at least one cell selected from the group consisting of a cell that was administered to the human, a progeny of a cell that was administered to the human, and a combination thereof.

In one embodiment, the persisting population of genetically engineered T cells comprises a memory T cell.

In one embodiment, the persisting population of genetically T engineered cells persists in the human for at least three months after administration.

In one embodiment, the persisting population of genetically engineered T cells persists in the human for at least four months, five months, six months, seven months, eight months, nine months, ten months, eleven months, twelve months, two years, or three years after administration.

The invention also provides a method of expanding a population of genetically engineered T cells in a human diagnosed with cancer, the method comprising administering to the human a cell genetically engineered to express a CAR, wherein the CAR comprises an antigen binding domain, a transmembrane domain, and an ICOS intracellular signaling domain, wherein the administered genetically engineered cell is selected from the group consisting of a Th17 cell and a Tc17 cell, further wherein the administered genetically engineered cell produces a population of progeny T cells in the human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 depicts the nucleotide sequence of SS1-ICOS-z (SEQ ID NO: 8). The cDNA sequence containing the SS 1-ICOS-z CAR was cloned into a third-generation lentiviral vector and expressed under the control of the EF-1 promoter (SEQ ID NO: 16). The SSI-ICOS-z contains the CD8 leader sequence, the SSI single chain fragment that recognized human mesothelin, the hinge region of the CD8α chain, the ICOS transmembrane and intracellular domains, and the TCR-z signal transduction domain.

FIG. 2, comprising FIG. 2A and FIG. 2B, depicts the generation of redirected Th17 cells. FIG. 2A depicts a schematic representation of a panel of chimeric receptors that contain the SS1 single chain fragment and differ in the intracellular domain. The novel ICOS-based CAR contains the TCR-zeta signal transduction domain with the ICOS intracellular domain in tandem. FIG. 2B depicts the results of a flow cytometry assay assessing the expression of SS1 scFv fusion proteins on human primary CD4+ T cells, normalized to 60% chimeric receptor expression for all receptors.

FIG. 5, comprising FIG. 5A through FIG. 5C, depicts the results of example experiments demonstrating that Th17 cells redirected with an ICOS-based CAR release high amounts of IL17-A and IFNγ but low amounts of IL-2 after antigen recognition in tumor cells. Th17 cells ($4\times10^5$, 60% chimeric receptor positive) were co-cultured with $2\times10^5$ K562, K562meso or the indicated tumor cells in culture media without Th17 polarizing cytokines or IL-2. Supernatants were obtained 24 h after coculture, and (A) IL-17A, (B) IL-2 and (C) IFNγ were analyzed by ELISA. Error bars indicate standard deviation (SD) in duplicate samples.

FIG. 6, comprising FIG. 6A illustrates the specific cytolysis, as determined using a flow cytometry-based assay. FIG. 6B depicts the ED50, as determined for each group using the four parameter logistic regression model. Representative of four experiments.

FIG. 7, comprising FIG. 7A depicts the mean tumor volume (+/−SEM) with n=9 for all groups. Peripheral blood from M108-bearing NSG mice treated with intratumoral injections of redirected Th17/Tc17 cells was obtained on day 51 after T cells infusion by intracardiac puncture. FIG. 7B illustrates the quantification for the presence of human CD4+ and CD8+ T cells by a FACS Trucount assay. Results are expressed as a mean absolute T-cell count per μL of peripheral blood +/−SD (n=9 for all groups).

FIG. 8, comprising FIG. 8A through 8D, demonstrate that $T_H17$ cells redirected with ICOSz showed increased expression of CD161. Redirected $T_H17$ cells were cocultured with irradiated APC expressing mesothelin. FIGS. 8A and 8B depict CD161 expression by CAR+CD4+ T cells in response to mesothelin-specific stimulation was analyzed by flow cytometry at indicated time points.

FIG. 9, comprising FIG. 9A and FIG. 9B, depicts the results of example experiments using CARs that include a combination of ICOS with other costimulatory domains. FIG. 9A depicts the ICOS-based CAR that contains the TCR-zeta signal transduction domain with the ICOS and the CD137 (4-1BB) costimulatory domains in triplicate. FIG. 9B depicts graphs that illustrate that the incorporation of the CD137 signaling domain in combination with ICOS did not alter the cytokine profile of Th17 cells redirected with a CAR containing only the ICOS costimulatory domain. Th17 cells ($4\times10^5$, 60% chimeric receptor positive) were co-cultured with $2\times10^5$ K562, K562meso or the indicated tumor cells in the absence of exogenous cytokines. Supernatants were obtained 24 h after co-culture, and IL-17A, IL-2 and IFNγ were analyzed by ELISA. Error bars indicate standard deviation (SD) in duplicate samples.

FIG. 10, comprising FIG. 10A depicts normalized Log 2 expression of selected differentially expressed genes (FC>2, FDR<0.05). Error bars represent SEM (3 different normal donors). FIG. 10B depicts a heat map of log 2 fold change in expression of T helper signature genes at 4h relative to 0h. FIG. 10C depicts a heat map of ingenuity pathway enrichment (IPA, p<0.01).

DETAILED DESCRIPTION

Figure 3:
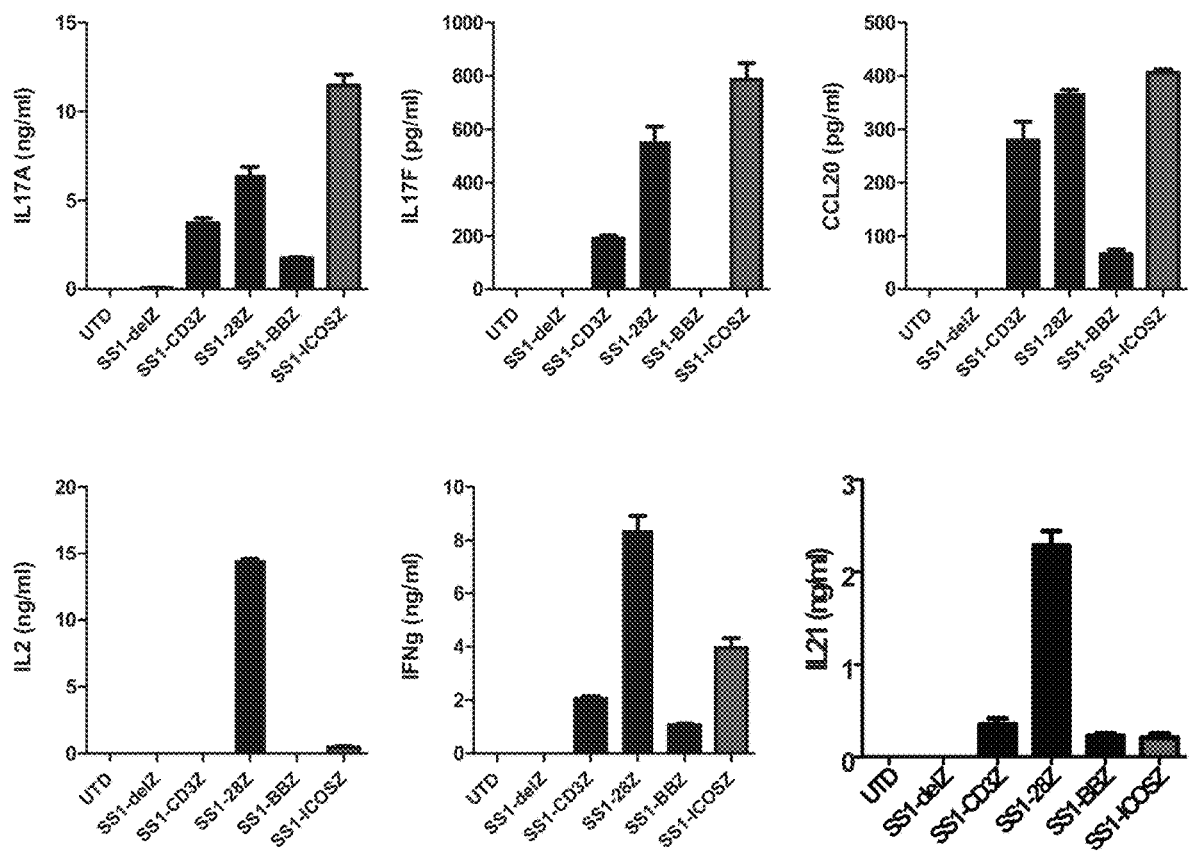
FIG. 3 depicts the results of example experiments demonstrating that Th17 cells redirected with an ICOS-based CAR release high amounts of IL17-A, IL-17F and CCL20 but low amounts of IL-2. Th17 cells ($4\times10^5$, 60% chimeric receptor positive) were cocultured with $2\times10^5$ K562meso cells in culture media without Th17 polarizing cytokines or IL-2. Supernatants were obtained 24 h after coculture, and cytokine production was analyzed by ELISA. Error bars indicate standard deviation (SD) in triplicate samples. Representative of three experiments.

The invention relates to compositions and methods for treating cancer, including, but not limited to, hematologic malignancies and solid tumors. The present invention relates to a strategy of adoptive cell transfer of Th17 cells transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity.

The present invention relates generally to the use of T cells genetically modified to express a desired CAR. T cells expressing a CAR are referred to herein as CAR T cells or CAR modified T cells. Preferably, the cell can be genetically modified to express an antibody binding domain on its surface, conferring novel antigen specificity that is MHC independent. In some instances, the T cell is genetically modified to express a CAR that combines an antigen recognition domain of a specific antibody with an intracellular domain of the CD3-zeta chain or FcγRI protein into a single chimeric protein.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In some embodiments, the extracellular domain also comprises a hinge domain. Preferably, the hinge domain comprises the CD8α hinge domain.

With respect to the cytoplasmic domain, the CAR of the invention can be designed to comprise the ICOS signaling domain by itself or be combined with any other desired cytoplasmic domain(s) useful in the context of the CAR of the invention. In one embodiment, the cytoplasmic domain of the CAR can be designed to further comprise the signaling domains of CD3-zeta, 4-1BB, and/or CD28. For example, the cytoplasmic domain of the CAR can include but is not limited to ICOS, CD3-zeta, 4-1BB and CD28 signaling modules and combinations thereof. Accordingly, the invention provides CAR T cells and methods of their use for adoptive therapy.

In one embodiment, the CAR T cells of the invention can be generated by introducing a lentiviral vector comprising a desired CAR, for example a CAR comprising anti-mesothelin, CD8α hinge, ICOS transmembrane domain, and human ICOS and CD3zeta signaling domains, into the cells. In one embodiment, the CAR T cells of the invention are able to replicate in vivo resulting in long-term persistence that can lead to sustained tumor control.

In another embodiment, the CAR T cells of the invention can be generated by transfecting an RNA encoding the desired CAR, for example a CAR comprising anti-mesothelin, CD8α hinge, ICOS transmembrane domain, and human ICOS and CD3zeta signaling domains, into the cells. In one embodiment, the CAR is transiently expressed in the genetically modified CAR T cells.

In one embodiment the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

In one embodiment, the invention relates to genetically modified Th17 cells expressing a CAR for the treatment of a patient having cancer. The present invention is based upon the finding that inclusion of the ICOS signaling domain within the cytoplasmic domain of a CAR increases Th17 persistence, increases IL-17 production, increases anti-tumor activity of Th17 cells, and reduces IL-2 production. In one embodiment, the reduction of IL-2 produced by Th17 cells expressing an ICOS containing CAR reduces proliferation of immunosuppressive Treg cells.

In yet another embodiment, the invention relates generally to the treatment of a patient at risk of developing cancer. The invention also includes treating a malignancy or an autoimmune disease in which chemotherapy and/or immunotherapy in a patient results in significant immunosuppression in the patient, thereby increasing the risk of the patient of developing cancer.

The invention includes using Th17 cells expressing an anti-mesothelin CAR, including both CD3-zeta and the ICOS costimulatory domain (also referred to as CAR-expressing Th17 cells). In one embodiment, the CAR-expressing Th17 cells of the invention can undergo robust in vivo expansion and can establish antigen-specific memory cells that persist at high levels for an extended amount of time in blood and bone marrow. In some instances, the CAR-expressing Th17 cells of the invention infused into a patient can eliminate cancerous cells in vivo in patients with a form of cancer. However, the invention is not limited to CAR-expressing Th17 cells. Rather, the invention includes any antigen binding domain fused with one or more intracellular domains selected from the group of a ICOS signaling domain, CD137 (4-1BB) signaling domain, a CD28 signaling domain, a CD3zeta signal domain, and any combination thereof.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Autoantigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addision's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject," "patient" and "individual" are used interchangeably herein and are intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating cancer as well as other diseases. The cancer may be a hematological malignancy, a solid tumor, a primary or a metastasizing tumor. Other diseases treatable using the compositions and methods of the invention include viral, bacterial and parasitic infections as well as autoimmune diseases.

In one embodiment, the invention provides a cell (e.g., Th17 cell) engineered to express a CAR wherein the CAR T cell exhibits an antitumor property. The CAR of the invention can be engineered to comprise an extracellular domain having an antigen binding domain fused to an intracellular signaling domain of the T cell antigen receptor complex zeta chain (e.g., CD3 zeta). The CAR of the invention when expressed in a T cell is able to redirect antigen recognition based on the antigen binding specificity. An exemplary antigen is mesothelin because this antigen is expressed on a large fraction of carcinomas. However, the invention is not limited to targeting mesothelin. Rather, the invention includes any antigen binding domain that when bound to its cognate antigen, affects a tumor cell so that the tumor cell fails to grow, is prompted to die, or otherwise is affected so that the tumor burden in a patient is diminished or eliminated. The antigen binding domain is preferably fused with an intracellular domain from one or more of a costimulatory molecule and a zeta chain. Preferably, the antigen binding domain is fused with one or more intracellular domains selected from the group of a ICOS signaling domain, a CD137 (4-1BB) signaling domain, a CD28 signaling domain, a CD3zeta signal domain, and any combination thereof.

In one embodiment, the CAR of the invention comprises an ICOS signaling domain. This is because the present invention is partly based on the discovery that CAR-mediated T-cell responses of Th17 cells can be further enhanced with the addition of costimulatory domains. For example, inclusion of ICOS signaling domain significantly increases IL-17 production, anti-tumor activity, and in vivo persistence of CAR expressing Th17 cells compared to an otherwise identical CAR T cell not engineered to express ICOS. Importantly, inclusion of the ICOS signaling domain within the CAR also significantly reduces IL-2 production. In one embodiment, reduction and/or elimination of IL-2 production is beneficial as the CAR would not trigger for regulatory T cell proliferation.

In some embodiments, the present invention is directed to a retroviral or lentiviral vector encoding a CAR that is stably integrated into a Th17 cell and stably expressed therein. In other embodiments, the present invention is directed to an RNA encoding CAR that is transfected into a Th17 cell and transiently expressed therein. Transient, non-integrating expression of CAR in a cell mitigates concerns associated with permanent and integrated expression of CAR in a cell.

Compositions

The present invention provides a chimeric antigen receptor (CAR) comprising an extracellular and intracellular domain. The extracellular domain comprises a target-specific binding element otherwise referred to as an antigen binding domain. In some embodiments, the extracellular domain also comprises a hinge domain. The intracellular domain or otherwise the cytoplasmic domain comprises a costimulatory signaling region and a zeta chain portion. The costimulatory signaling region refers to a portion of the CAR comprising the intracellular domain of a costimulatory molecule. Costimulatory molecules are cell surface molecules other than antigen receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The present invention includes retroviral and lentiviral vector constructs expressing a CAR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the CAR.

Preferably, the CAR comprises an extracellular domain, a transmembrane domain and a cytoplasmic domain. The extracellular domain and transmembrane domain can be derived from any desired source of such domains.

In some instances, the hinge domain of the CAR of the invention comprises the CD8α hinge domain. In one embodiment, the CD8 hinge domain comprises the nucleic acid sequence of SEQ ID NO: 4. In another embodiment, the CD8 hinge domain comprises the amino acid sequence encoded by the nucleic acid sequence of SEQ ID NO: 4.

Antigen Binding Domain

In one embodiment, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding domain that specifically binds to an antigen on a tumor cell. In the context of the present invention, "tumor antigen" or "hyperporoliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding domain of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, and the like.

Depending on the desired antigen to be targeted, the CAR of the invention can be engineered to include the appropriate antigen bind moiety that is specific to the desired antigen target. For example, if mesothelin is the desired antigen that is to be targeted, an antibody for mesothelin can be used as the antigen bind moiety for incorporation into the CAR of the invention.

In one embodiment, the antigen binding domain portion of the CAR of the invention targets mesothelin. Preferably, the antigen binding domain portion in the CAR of the invention is the SS1 scFv that recognizes human mesothelin, wherein the nucleic acid sequence of the SS1 scFv comprises the sequence set forth in SEQ ID NO: 3. In another embodiment, the SS1 scFv portion of the CAR of the invention comprises the amino acid sequence encoded by the nucleic acid sequence set forth in SEQ ID NO: 3.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, ICOS. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Preferably, the transmembrane domain in the CAR of the invention comprises the ICOS transmembrane domain. In one embodiment, the ICOS transmembrane domain comprises the nucleic acid sequence of SEQ ID NO: 5. In another embodiment, the ICOS transmembrane domain comprises the amino acid sequence encoded by the nucleic acid sequence of SEQ ID NO: 5.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3-zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention is exemplified primarily with ICOS as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of ICOS. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of ICOS and 4-1BB.

In one embodiment, the cytoplasmic domain in the CAR of the invention is designed to comprise the signaling domain of ICOS and the signaling domain of CD3-zeta, wherein the signaling domain of ICOS comprises the nucleic acid sequence set forth in SEQ ID NO: 6 and the signaling domain of CD3-zeta comprises the nucleic acid sequence set forth in SEQ ID NO: 7.

In one embodiment, the cytoplasmic domain in the CAR of the invention is designed to comprise the signaling domain of ICOS and the signaling domain of CD3-zeta, wherein the signaling domain of ICOS comprises the amino acid sequence encoded by the nucleic acid sequence set forth in SEQ ID NO: 6 and the signaling domain of CD3-zeta comprises the amino acid sequence encoded by the nucleic acid sequence set forth in SEQ ID NO: 7.

Vectors

The present invention encompasses a DNA construct comprising sequences of a CAR, wherein the sequence comprises the nucleic acid sequence of an antigen binding domain operably linked to the nucleic acid sequence of an intracellular domain. An exemplary intracellular domain that can be used in the CAR of the invention includes but is not limited to the intracellular domain of CD3-zeta, ICOS, CD28, 4-1BB, and the like. In some instances, the CAR can comprise any combination of CD3-zeta, ICOS, CD28, 4-1BB, and the like.

In one embodiment, the CAR of the invention comprises anti-mesothelin scFv (e.g. SS1 scFv), human CD8 hinge, ICOS transmembrane domain, and human ICOS and CD3zeta signaling domains. In one embodiment, the CAR of the invention comprises the nucleic acid sequence set forth in SEQ ID NO: 8. In another embodiment, the CAR of the invention comprises the amino acid sequence encoded by the nucleic acid sequence set forth in SEQ ID NO: 8.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In one embodiment, the genetically modified T cells of the invention are modified through the introduction of RNA. In one embodiment, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. For example, the template for the RNA CAR comprises an extracellular domain comprising a single chain variable domain of an anti-tumor antibody; a transmembrane domain comprising the hinge and transmembrane domain of CD8a; and a cytoplasmic domain comprises the signaling domain of CD3-zeta and the signaling domain of ICOS.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, t is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion, a source of T cells is obtained from a subject. Examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations.

T cells for stimulation can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Th17/Tc17 Cells

In one embodiment, the present invention is directed to genetically modified Th17 cells. Th17 cells that have been modified to express a CAR of the invention are redirected towards a specific antigen (e.g. mesothelin), and thus can be used to treat cancers associated with the specific antigen. The present invention is based on the surprising discovery that incorporation of the ICOS signaling domain within the cytoplasmic domain of the CAR increases Th17 persistence, increases IL-17 production, increases anti-tumor activity, and decreases IL-2 production.

T helper cells (also known as effector T cells or Th cells) are a sub-group of lymphocytes (a type of white blood cell or leukocyte) that plays an important role in establishing and maximizing the capabilities of the immune system and in particular in activating and directing other immune cells. Different types of Th cells have been identified that originate in outcome of a differentiation process and are associated with a specific phenotype. Following T cell development, matured, naive (meaning they have never been exposed to the antigen to which they can respond) T cells leave the thymus and begin to spread throughout the body. Naive T cells are known to differentiate into a T-helper 1 (Th1), T-helper 2 (Th2), T-helper 17 (Th17) or regulatory T cell (Treg) phenotype.

Each of these Th cell types secretes cytokines, proteins or peptides that stimulate or interact with other leukocytes, including Th cells. However, each cell type has a peculiar phenotype and activity that interferes and often conflict with the other.

Th1, Th2, and Th17 (inflammatory T-helper or inflammatory Th), promote inflammation responses trough secretion of pro-inflammatory cytokines, such as IL-1, IL-6, TNF-α, IL-17, IL21, IL23, and/or through activation and/or inhibition of other T cell including other Th cells (for example Th1 cell suppresses Th2 and Th17, Th2 suppresses Th1 and Th17). Tregs instead, are a component of the immune system that suppresses biological activities of other cells associated to an immune response. In particular, Tregs can secrete immunosuppressive cytokines TGF-β and Interleukin 10, and are known to be able to limit or suppress inflammation.

Th17 cells or otherwise cells exhibiting Th17 cell phenotype may have a variety of specific phenotypic properties, depending on the conditions employed. Such phenotypic properties include production of IL-17A and IFNγ. Moreover, expanded Th17 cells continue to produce both IL-17A and IFNγ event after their primary expansion. In some instances, Th17 cells coexpressed both RORγt and T-bet, transcription factors that regulate Th17 and Th1 cell development, respectively. In some instances, expanded T cells coexpressed IL-23R and CD161 on their cell surface, phenotypic markers associated with umbilical cord Th17 cells. In some instances, Th17 cells expressed RORγt.

In one embodiment, the invention provides a purified population of ICOS+CD28+ umbilical cord blood Th17 precursor cells that secrete elevated levels of CCL20, IL-17F and IFNγ upon stimulation. The cells of the present invention can be used in clinical applications for the design of immunotherapies for patients with cancer, infectious disease and autoimmunity.

Activation and Expansion of Th17 Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of Th17 cells, cells can be contacted with an anti-CD3 antibody and an anti-ICOS antibody. Th17 cells can also be stimulated with ICOS ligand (ICOSL)-expressing artificial antigen presenting cells (aAPCs). Stimulation can be performed in the presence of Th17-polarizing cytokines. An example of Th17-polarizing cytokines include but is not limited to IL-6, IL-1β and IL-23 cytokines and neutralizing IFNγ and IL-4 antibodies.

A T cell may be stimulated by contacting an agent with a cell surface moiety on the T cell. In one aspect of the present invention, antibodies to CD3 and ICOS are loaded onto an aAPC. Further, stimulation may include any ligand that binds the TCR/CD3 complex and initiates a primary stimulation signal. This ligand may be utilized as a primary activation agent loaded onto or expressed by the aAPC. Any ligand that binds ICOS and initiates the ICOS signal transduction pathway, thus causing co-stimulation of the cell with a CD3 ligand and enhancing activation of a population of T cells, is an ICOS ligand and accordingly, is a co-stimulatory agent.

T cells can be exposed to a bead comprising a first agent that binds the TCR/CD3 complex and initiates a primary stimulation signal and a second agent that binds ICOS and initiates the ICOS signal transduction pathway, thus causing co-stimulation of the cell with a CD3 ligand and enhancing activation of a population of T cells.

Stimulated cells are activated as shown by the induction of signal transduction, expression of cell surface markers and/or proliferation. Markers appropriate for Th17 cells include but are not limited to their capacity to secrete heightened levels of IL-17A, IL-17F and CCL20. Moreover, cells generated and expanded according to the ICOS costimulation method not only exhibit elevated production of Th17-associated cytokines but also exhibit elevated secretion of IFNγ, TNFα and IL-21 compared to CD28 costimulated cells.

In the context of generating Th17 cells by way of stimulating ICOS on T cells, an aAPC can be engineered to comprise a first agent that binds to TCR/CD3 complex of the T cell and a second agent that binds ICOS, the aAPC can further be engineered to comprise a cytokine that promotes Th17 differentiation. Exemplary Th17 differentiating cytokines include but are not limited to IL-2, IL-6, IL-23, and IL-1.

Accordingly, T cell stimulation may include an aAPC that has been genetically modified to express stimulatory agents, co-stimulatory agents, and/or cytokines as well as other polypeptides. The aAPC can be engineered to express and secrete any desirable cytokine that promotes Th17 differentiation using the methods disclosed herein or known methods in the art for genetically modifying a cell. The cytokine can be a full-length, fragment, homologue, variant or mutant of the cytokine. A cytokine includes a protein that is capable of affecting the biological function of another cell. A biological function affected by a cytokine can include, but is not limited to, cell growth, cell differentiation or cell death. In stimulating the stimulation of Th17 cells, the cytokine can bind to a specific receptor on the surface of cell, thereby promoting Th17 differentiation. A preferred cytokine includes, among others, a hematopoietic growth factor, an interleukin, an interferon, an immunoglobulin superfamily molecule, a tumor necrosis factor family molecule and/or a chemokine. A cytokine includes but is not limited to granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interleukin-23 (IL-23), interferon alpha (IFNα), interferon beta (IFNβ), interferon gamma (IFNγ), and IGIF, among many others. A more preferred cytokine includes a cytokine that promotes Th17 differentiation including but not limited to IL-2, IL-6, IL-1 (e.g., IL-1β). One skilled in the art would appreciate, once armed with the teachings provided herein, that the invention encompasses any Th17 differentiation promoting cytokine, such as those known in the art, as well as any discovered in the future.

In addition to engineering an aAPC to comprise a Th17 differentiation promoting cytokine, the aAPC can be engineered to comprise an inhibitory molecule that can block a cytokine that interferes with the Th17 differentiation process. For example, the aAPC can be engineered to secrete a neutralizing antibody than can inhibit a cytokine that interferes with Th17 differentiation. A cytokine that interferes with Th17 differentiation process includes but is not limited to IFNγ and IL-4.

When the aAPC has been engineered to express a desired cytokine that promotes Th17 differentiation and/or inhibitor of a cytokine that interferes with Th17 differentiation, a method for activating and/or stimulating a population of T cells to promote Th17 differentiation in the absence of exogenously added cytokines is provided. Further, such Th17 differentiation may occur in vivo.

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-ICOS antibody or antigen-binding fragment thereof; and both agents are co-immobilized to the same bead in equivalent molecular amounts. In one embodiment, a 1:1 ratio of each antibody bound to the beads for Th17 growth is used. In certain aspects of the present invention, a ratio of anti CD3:ICOS antibodies bound to the beads is used such that an increase in Th17 cell expansion is observed as compared to the expansion observed using a ratio of 1:1. In one embodiment, the ratio of CD3:ICOS antibody bound to the beads ranges from 100:1 to 1:100 and all integer values there between. In one aspect of the present invention, more anti-ICOS antibody is bound to the particles than anti-CD3 antibody, i.e., the ratio of CD3:ICOS is less than one. In certain embodiments of the invention, the ratio of anti ICOS antibody to anti CD3 antibody bound to the beads is greater than 2:1. In one particular embodiment, a 1:100 CD3:ICOS ratio of antibody bound to beads is used. In another embodiment, a 1:75 CD3:ICOS ratio of antibody bound to beads is used. In a further embodiment, a 1:50 CD3:ICOS ratio of antibody bound to beads is used. In another embodiment, a 1:30 CD3:ICOS ratio of antibody bound to beads is used. In one preferred embodiment, a 1:10 CD3:ICOS ratio of antibody bound to beads is used. In another embodiment, a 1:3 CD3:ICOS ratio of antibody bound to the beads is used. In yet another embodiment, a 3:1 CD3:ICOS ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-ICOS-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-ICOS are attached to contact the T cells. In one embodiment the cells (for example, $10^4$ to $10^9$ T cells) and beads (for example, paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (Th, $CD4^+$) that is greater than the cytotoxic or suppressor T cell population (Tc, $CD8^+$). Accordingly, depending on the purpose of treatment, infusing a subject with a T cell population comprising predominately of Th cells may be advantageous. Similarly, if an antigen-specific subset of Tc cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Those of ordinary skill in the art will readily appreciate that the cell stimulation methodologies described herein may be carried out in a variety of environments (i.e., containers). For example, such containers may be culture flasks, culture bags, or any container capable of holding cells, preferably in a sterile environment. In one embodiment of the present invention a bioreactor is also useful. For example, several manufacturers currently make devices that can be used to grow cells and be used in combination with the methods of the present invention. See for example, patents covering bioreactors such as U.S. Pat. Nos. 6,096,532; 5,985,653; 5,888,807; 5,190,878, each of which is incorporated herein by reference in their entirety.

Therapeutic Application

The present invention encompasses a cell (e.g., Th17 cell) modified to express a CAR that combines an antigen recognition domain of a specific antibody with an intracellular domain of CD3-zeta, CD28, 4-1BB, ICOS, or any combinations thereof. Therefore, in some instances, the transduced Th17 cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3-zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, it was unexpected that the inclusion of the ICOS signaling domain within the CARs expressed by genetically modified Th17 cells resulted in increased Th17 persistence and increased anti-tumor activity. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding domain in the CAR. For example, genetically modified Th17 cells which express an anti-mesothelin CAR elicits an immune response specific against cells expressing mesothelin.

While the data disclosed herein specifically disclose lentiviral vector comprising SS1 scFv, human CD8α hinge, ICOS transmembrane domain, and ICOS and CD3zeta signaling domains, the invention should be construed to include any number of variations for each of the components of the construct as described elsewhere herein. That is, the invention includes the use of any antigen binding domain in the CAR to generate a CAR-mediated T-cell response specific to the antigen binding domain. For example, the antigen binding domain in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, meningioma, neuroblastoma, retinoblastoma and brain metastases).

In one embodiment, the antigen bind moiety portion of the CAR of the invention is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR can be designed to target mesothelin to treat mesothelioma, pancreatic cancer, ovarian cancer, and the like. In another embodiment, the CAR can be designed to target CD33/IL3Ra to treat acute myelogenous leukemia and the like. In a further embodiment, the CAR can be designed to target c-Met to treat triple negative breast cancer, non-small cell lung cancer, and the like.

In one embodiment, the CAR can be designed to target PSMA to treat prostate cancer and the like. In another embodiment, the CAR can be designed to target Glycolipid F77 to treat prostate cancer and the like. In a further embodiment, the CAR can be designed to target EGFRvIII to treat gliobastoma and the like.

In one embodiment, the CAR can be designed to target GD-2 to treat neuroblastoma, melanoma, and the like. In another embodiment, the CAR can be designed to target NY-ESO-1 TCR to treat myeloma, sarcoma, melanoma, and the like. In a further embodiment, the CAR can be designed to target MAGE A3 TCR to treat myeloma, sarcoma, melanoma, and the like.

However, the invention should not be construed to be limited to solely to the antigen targets and diseases disclosed herein. Rather, the invention should be construed to include any antigenic target that is associated with a disease where a CAR can be used to treat the disease.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Redirection of Th17 Cells with a CAR Containing the ICOS Costimulatory Domain Enhances Function, Anti-Tumor Activity and Persistence of Th17 Cells Adoptive transfer of large numbers of Th17 cells polarized and expanded in vitro is an attractive therapy for the treatment of cancer. CD278, the inducible costimulator (ICOS) has been shown to be critical for the sustained expansion of human Th17 cells after their primary activation. It was analyzed whether incorporation of the ICOS intracellular domain in a chimeric antigen receptor can promote Th17 phenotype after antigen priming and enhance the antitumor activity of engineered T cell therapies.

The materials and methods employed in these experiments are now described.

Isolation, Polarization, Transduction and Expansion of Th17 and Tc17 Cells

Blood samples were obtained from the Human Immunology Core of the University of Pennsylvania. Peripheral blood $CD4^+$ and $CD8^+$ T cells were negatively isolated using RosetteSep Kits (Stem cell Technologies). Cells were cultured in RPMI 1640 media supplemented with 10% FCS, 100-U/ml penicillin, 100 µg/ml streptomycin sulfate, 10 mM Hepes in a 37° C. and 5% $CO_2$ incubator. For stimulation, $CD4^+$ and $CD8^+$ T cells were cultured with activating beads coated with antibodies to CD3 and ICOS at a 1:3 cell to bead ratio. For Th17 and Tc17 polarization, IL-1b (10 ng/ml), IL-6 (10 ng/ml), IL-23 (20 ng/ml), and neutralizing antibodies (10 mg/ml) against IL-4 and IFN-γ (eBioscience) were added at day 0 and maintained throughout the experiment. All experiments were conducted with fetal calf serum containing endogenous sources of TGF-b. Human IL-2 (Chiron) was added 3 days after activation to a final concentration of 50 IU/ml. Approximately 24 h after activation, T cells were transduced with lentiviral vectors at an MOI of 5. Cells were counted and fed every 2 days and once T cells appeared to rest down, as determined by both decreased growth kinetics and cell size, they were either used for functional assay or cryopreserved.

T Cell Proliferation Assay

Cryopreserved T cells transduced with SS1 fusion proteins were thawed, washed, and placed in culture for 12 h. T cells ($4\times10^5$) were co-cultured with $2\times10^5$ K562.meso. At indicated time points, viable cells were counted by trypan blue exclusion. Cells were fed every 2 days with fresh media without exogenous cytokines.

Cytokine Production and Intracellular Staining of Restimulated T Cells

Cryopreserved T cells transduced with SS1 fusion proteins were thawed, washed, and placed in culture for 16 h. Then, expression of the SS1 scFv fusion proteins was examined in T cells and normalized to 60% chimeric receptor expression for all receptors. T cells ($4\times10^5$) were then co-cultured with $2\times10^5$ K562, K562.meso, or tumor cells and supernatants were harvested 24 h later. Concentrations of IL-17A, IL17-F, IL-2, IFN-γ, TNF-α and CCL20 were determined using the DuoSet® ELISA Development Systems. Concentrations of IL-21 were determined using Human IL-21 ELISA Ready-SET-Go! Set.

Antibodies

The following conjugated antibodies were purchased from BD Biosciences: anti-CD8 (FICT), anti-CD4 (PerCp-Cy5.5), anti-CCR7 (PE). Anti-CD45RO (Alexa Fluor 647) was purchased from Biolegend. Anti-CD27 (V450) and anti-CD4 (APC-H7) were purchased from BD Bioscience. Anti-CD161 PE was purchased from R&D. The biotinylated F(ab')2 fragment of goat anti-mouse IgG sera (specific for scFvs of murine origin) was purchased from Jackson ImmunoResearch. Streptavidin (eFluor 710) was purchased from eBioscience, and streptavidin (V450) was purchased BD Biosciences.

Flow Cytometry-Based Assay to Quantify Cell-Mediated Cytolysis

Target cells (L55) were stained with CFSE and seeded at 50,000 cells/well in a 96 well/plate. Cryopreserved Th17 and Tc17 cells transduced with SS1 fusion proteins were thawed, washed, and placed in culture for 16 h. Then, effectors and CFSE-labeled target cells were co-cultured at a range of E:T in duplicate. Cultures were incubated for 4 h at 37° C. under 5% $CO_2$. Total cells were then collected by trypsinization and washed. T cells were then stained with an anti-CD45 antibody for 30 minutes. After washing, the DNA intercalating dye 7AAD was added to the samples to distinguish dead from live cell events. Finally, cells were washed and re-suspended in 0.4 ml of 1% HuSA PBS and counting beads. After staining, samples were placed on ice and data collected immediately on a LSRII Flow cytometer. Four thousand beads were collected for each sample.

Flow Cytometry Analysis

For assessment of surface expression, cells were stained at the indicated time points. Expression of the various SS1 scFv fusion proteins on T cells was detected using biotinylated goat anti-mouse IgG followed by staining with either streptavidin (V450) or streptavidin (eFluor 710). Samples were analyzed in the LSRII flow cytometer using the DiVa software (BD Biosciences), and results were evaluated using the FlowJo software (TreeStar).

Mice

The University of Pennsylvania Institutional Animal Care and Use Committee approved all animal experiments. NSG mice were purchased from The Jackson Laboratory and bred in the vivarium at the University of Pennsylvania. The mice were housed under specific pathogen-free conditions in microisolator cages and given ad libitum access to autoclaved food and acidified water.

In Vivo Assessment of Anti-Mesothelin CAR T Cells

Xenograft tumors were established by subcutaneous injection of $5\times10^6$ M108 cells in the presence of a 50% solution of Matrigel (BD Biosciences) in PBS. M108 tumors were allowed to grow in NSG mice for 8 weeks.

To evaluate the intratumoral efficacy of redirected Th17-Tc17, the mice were treated with 2 intratumoral injections of $10\times10^6$ T cells (Th17:Tc17 at 1:1 ratio) or PBS on days 61 and 67.

Tumor dimensions were measured with calipers, and tumor volumes calculated using the formula $V=\frac{1}{2}\times L\times W\times W$, where L is length (longest dimension) and W is width (shortest dimension). Peripheral blood was obtained on days 21 and 51 after treatment from retro-orbital bleeding or intracardiac puncture respectively, and stained for the presence of human CD45, CD4, and CD8 T cells. After gating on the human $CD45^+$ population, the $CD4^+$ and $CD8^+$ subsets were quantified using TruCount tubes (BD Biosciences).

Sample Collection

Th17 cells from three different normal donors and redirected with SS1-28z, SS1-BBz and SS1-ICOSz were thaw and cultured in RMPI 1640 media supplemented with 10% FCS overnight. Then, redirected Th17 cells were stimulated with immobilized yeast-derived recombinant Mesothelin. Cell pellets were collected and frozen on day 0 prior to stimulation, and 4 h, 8 h, 24 h and 4 days upon antigen recognition.

Microarray Target Preparation and Hybridization

Microarray services were provided by the UPenn Microarray Facility, including quality control tests of the total RNA samples by Agilent Bioanalyzer and Nanodrop spectrophotometry. All protocols were conducted as described in the Affymetrix GeneChip Expression Analysis Technical Manual. Briefly, 100 ng of total RNA was converted to first-strand cDNA using reverse transcriptase primed by poly(T) and random oligomers that incorporated the T7 promoter sequence. Second-strand cDNA synthesis was followed by in vitro transcription with T7 RNA polymerase for linear amplification of each transcript, and the resulting cRNA was converted to cDNA, fragmented, assessed by Bioanalyzer, and biotinylated by terminal transferase end labeling. cRNA yields ranged from 36-89 ug, and cDNA was added to Affymetrix hybridization cocktails, heated at 99° C. for 5 min and hybridized for 16 h at 45° C. to Human Gene 1.0ST GeneChips (Affymetrix Inc., Santa Clara Calif.). The microarrays were then washed at low (6×SSPE) and high (100 mM MES, 0.1M NaCl) stringency and stained with streptavidin-phycoerythrin. Fluorescence was amplified by adding biotinylated anti-streptavidin and an additional aliquot of streptavidin phycoerythrin stain. A confocal scanner was used to collect fluorescence signal after excitation at 570 nm.

Data Analysis

Affymetrix Command Console and Expression Console were used to quantitate expression levels for targeted genes; default values provided by Affymetrix were applied to all analysis parameters. Border pixels were removed, and the average intensity of pixels within the 75th percentile was computed for each probe. The average of the lowest 2% of probe intensities occurring in each of 16 microarray sectors was set as background and subtracted from all features in that sector. Probe sets for positive and negative controls were examined in Expression Console, and Facility quality control parameters were confirmed to fall within normal ranges. Probes for each targeted gene were averaged and inter-array normalization performed using the RMA algorithm.

The results of the experiments are now described.

Results

Th17 polarized cells were engineered to express a single-chain variable fragment that binds mesothelin (SS1) fused to the T cell receptor-zeta signal transduction domain in tandem with the CD28, CD137 (41BB) or CD278 (ICOS) intracellular domains. The cDNA sequence containing the SS1-ICOS-z CAR was cloned into a third-generation lentiviral vector and expressed under the control of the EF-1 promoter. The SS1-ICOS-z contains the CD8 leader sequence, the SS1 single chain fragment that recognized human mesothelin, the hinge region of the CD8α chain, the ICOS transmembrane and intracellular domains, and the TCR-z signal transduction domain. (FIG. 1).

Sequence Identifiers

| SEQ ID NO: # | IDENTITY |
|---|---|
| SEQ ID NO: 1 | EF-1 promoter (nucleic acid sequence) |
| SEQ ID NO: 2 | CD8a leader (nucleic acid sequence) |
| SEQ ID NO: 3 | SS1 (nucleic acid sequence) |
| SEQ ID NO: 4 | CD8a hinge (nucleic acid sequence) |
| SEQ ID NO: 5 | ICOS transmembrane domain (nucleic acid sequence) |
| SEQ ID NO: 6 | ICOS intracellular domain (nucleic acid sequence) |
| SEQ ID NO: 7 | CD3z (nucleic acid sequence) |
| SEQ ID NO: 8 | SS1-ICOS-z CAR (nucleic acid sequence) |
| SEQ ID NO: 9 | CD8a leader (amino acid sequence) |
| SEQ ID NO: 10 | SS1 (amino acid sequence) |
| SEQ ID NO: 11 | CD8a hinge (amino acid sequence) |
| SEQ ID NO: 12 | ICOS transmembrane domain (amino acid sequence) |
| SEQ ID NO: 13 | ICOS intracellular domain (amino acid sequence) |
| SEQ ID NO: 14 | CD3z (amino acid sequence) |
| SEQ ID NO: 15 | SS1-ICOS-z CAR (amino acid sequence) |
| SEQ ID NO: 16 | EF1α promoter driving SS1-ICOSCD3z |

Th17 cells were transduced with chimeric receptors that contain the SS1 single chain fragment, but differ in their intracellular domains. The panel of chimeric receptors used in the experiments includes SS1-CD3z, SS1-28z, SS1-BBz, and the novel SS1-ICOSz construct. (FIG. 2). Expression of the chimeric receptor on untransduced and transduced cells was evaluated by flow cytometry (FIG. 2B).

Figure 4:
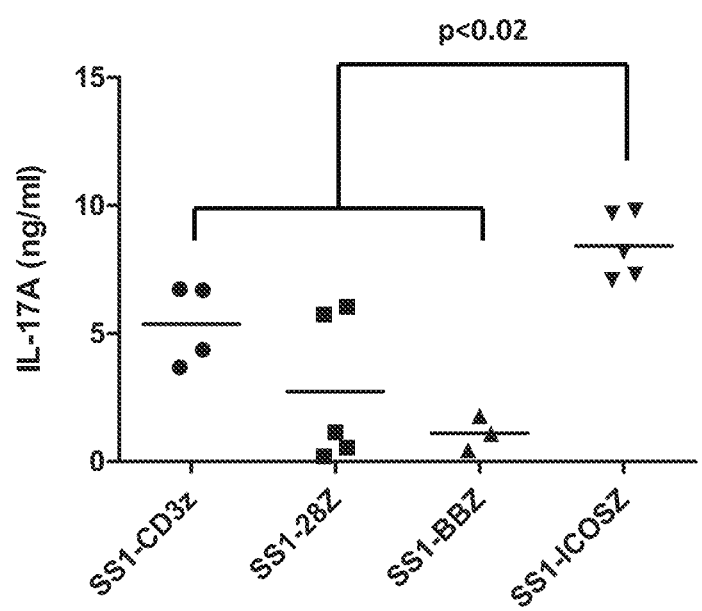
FIG. 4 depicts the results of an example experiment demonstrating that ICOS augments IL-17A production by human Th17 cells. $T_H17$ cells from 5 different normal donors ($4\times10^5$, 60% chimeric receptor positive) were cocultured with $2\times10^5$ K562meso cells in culture media without Th17 polarizing cytokines or IL-2. Supernatants were obtained 24 h after coculture, and IL-17A production was analyzed by ELISA.

CAR transduced Th17 cells were co-cultured with K562-meso cells in media without the Th17 polarizing cytokines or IL-2. Cytokine production was analyzed by ELISA 24 hours after co-culture. Th17 cells transduced with the ICOS containing CAR released increased amounts of IL-17A, IL-17F and CCL20 compared to CARs that do not contain the ICOS domain. Further, Th17 cells transduced with the ICOS containing CAR released very low levels of IL-2 (FIG. 3). By contrast, Th17 cells redirected with the SS1-28-z, secreted higher amounts of IL-2 and IFN-γ but nominal levels of IL-17A and IL-17F. Further, when Th17 cells from five different human donors were transduced with the various CARs, cells transduced with SS1-ICOSz displayed significantly increased IL-17 production 24 hours post co-culture with K562-meso cells (FIG. 4).

Th17 cells transduced with the various CARs were co-cultured with K562, K562-meso, or with one five different tumor cell lines (M108, L55, ASPC1, BxPC3, and Ov79) in culture media without Th17 polarizing cytokines or IL-2. After 24 hours of co-culture, Th17 cells transduced with the SS1-ICOSz CAR released increased amounts of IL-17A and decreased amounts of IL-2 compared to cells transduced with SS1-28z (FIG. 5).

Figure 8C:
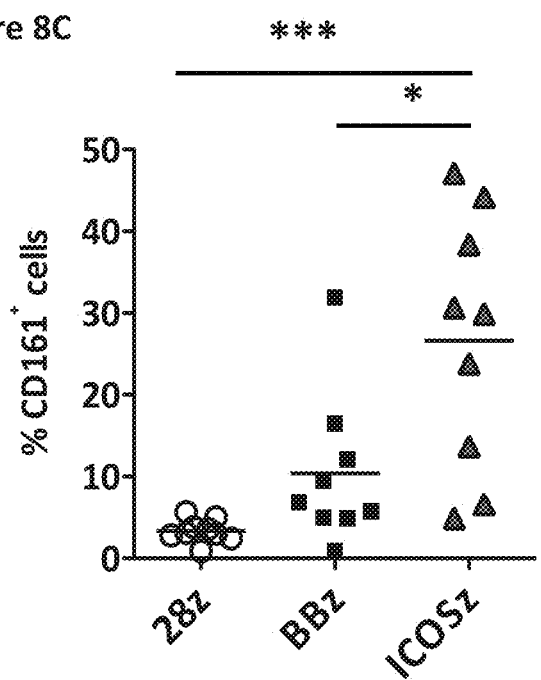
FIG. 8C depicts the percentage of CAR+CD4+ T cells expressing CD161 at day 8 in several different normal donors (n=9) is plotted.
Figure 8D:
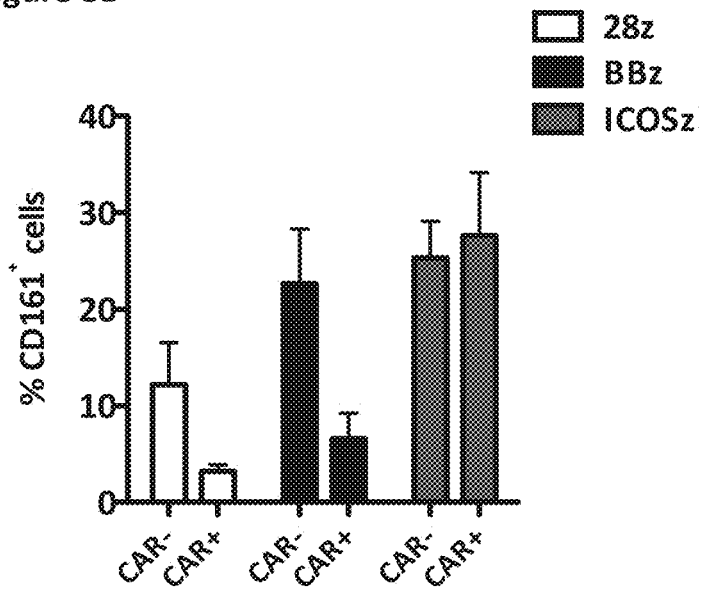
FIG. 8D depicts CD161 expression in CAR+ and CAR− cells at day 8. Error bars represent SEM (5 different normal donors).

CAR transduced Th17 cells were also evaluated for their expression of CD161. CD161 is a marker that is indicative of the Th17 phenotype. Flow cytometry shows that Th17 cells transduced with the ICOS containing CAR exhibited greater number of CD161+ cells compared to SS1-28z and SS1-BBz constructs (FIG. 8). By contrast, Th17 cells transduced with SS1-28-z had low CD161 expression.

Figures 6A, 6B:
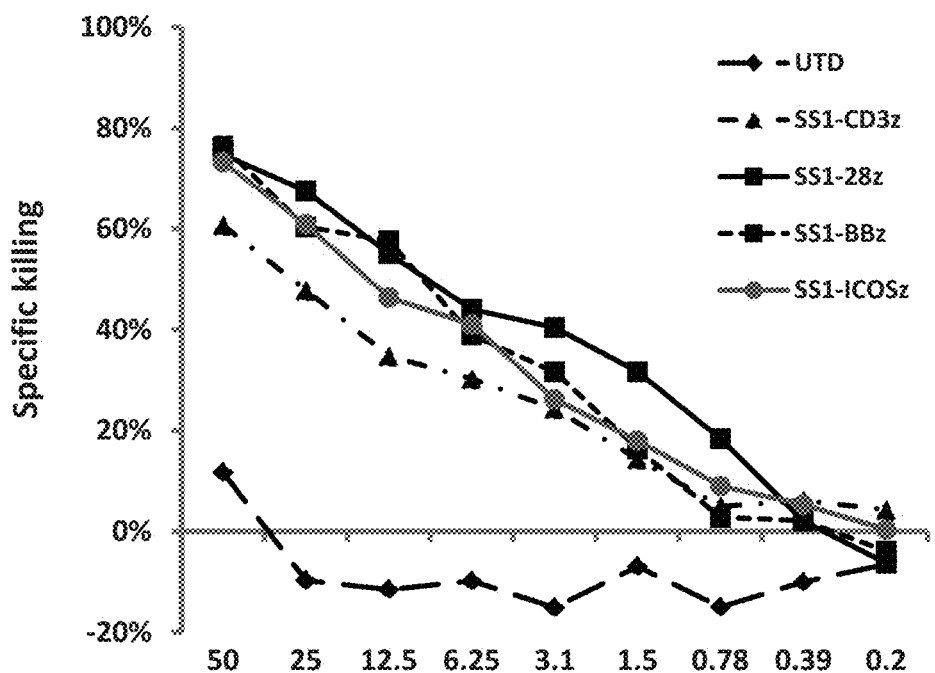
FIG. 6A and FIG. 6B, depicts the results of example experiments assessing the cytolytic activity of Th17/Tc17 cells redirected with chimeric receptors. A mix of Tc17 and Th17 cells (at a 4:1 ratio) were co-cultured with L55 target cells stained with CFSE at the indicated effector-target (E:T) ratios for 4 h.

To measure the cytolytic activity of Th17/Tc17 cells redirected with chimeric receptors, Tc17 and Th17 cells (at a 4:1 ratio) were co-cultured with L55 target cells for 4 hours. Specific cytolysis was determined using a flow-cytometry based assay, which demonstrated that Th17/Tc17 cells redirected with the SS1-ICOSz CAR effectively killed tumor cells at a wide range of effector to target cell ratios (FIG. 6A). The ED50 for each group was determined using a logistic regression model, which showed that the ED50 of the SS1-ICOSz group was 6.857 (FIG. 6B).

Figure 7A:
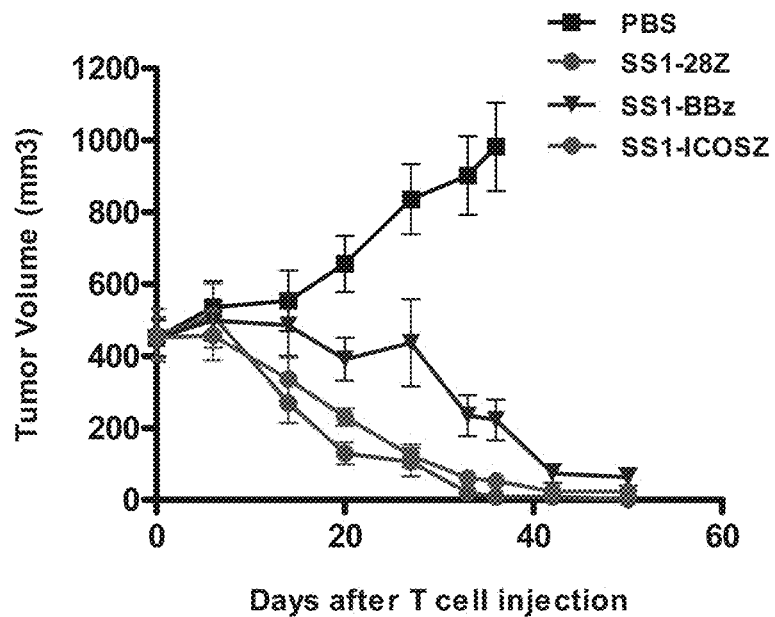
FIG. 7A and FIG. 7B, depicts the results of example experiments demonstrating that Th17/Tc17 cells redirected with an ICOS-based CAR eradicate large pre-established tumors and show enhanced persistence in vivo. Human primary M108 tumors were established in the flanks of NSG mice. After 8 weeks, when the tumors reached a volume of 500 mm³, mice were treated with 2 intratumoral injections of $10\times10^6$ Th17/Tc17 cells (80%/60% chimeric receptor-positive) or PBS on days 61 and 67.
Figure 7B:
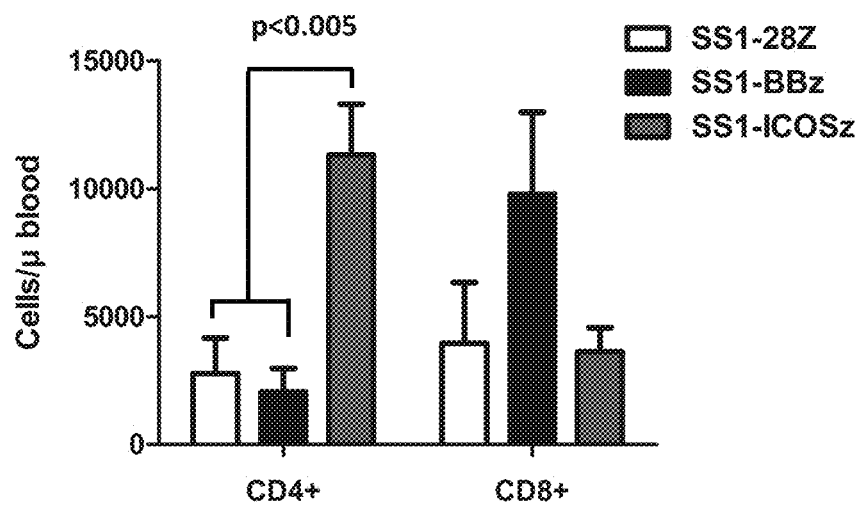

To further evaluate the anti-tumor activity of redirected Th17/Tc17 cells, mice with pre-established M108 tumors were treated with intratumoral injections of Th17/Tc17 cells or PBS. Tumor volume was reduced in mice treated with genetically redirected Th17/Tc17 cells, including those transduced with SS1-ICOSz CAR (FIG. 7A). When transferred into NSG mice with large vascularized pre-established tumors, Th17/Tc17 cells redirected with SS1-ICOS-z mediated enhanced antitumor responses, with 70% of mice showing complete remission. The peripheral blood from the M108-bearing mice was quantified for the presence of human CD4+ and CD8+ T cells by FACS. FACS analysis showed that human CD4+ counts were significantly higher in mice treated with Th17/Tc17 cells transduced with SS1-ICOSz (FIG. 7B). Importantly, incorporation of the ICOS intracellular domain in the CAR significantly increased Th17 cell persistence post infusion when compared with the incorporation of CD28 or 41BBz intracellular domains, although Tc17 cell persistence was similar in all groups.

ICOS based CARs that included a combination of ICOS and other costimulatory domains were also evaluated. A construct was designed and constructed to contain the CD3 zeta signal transduction domain along with the ICOS and CD137 (4-1BB) costimulatory domains (FIG. 9A). Th17 cells were transduced to express a CAR that contained the ICOS costimulatory domain, with or without the inclusion of the CD137 (4-1BB) costimulatory domain. Transduced Th17 cells ($4\times10^5$, 60% chimeric receptor positive) were co-cultured with $2\times10^5$ K562, K562meso or the indicated tumor cells in the absence of exogenous cytokines. Supernatants were obtained 24 h after co-culture, and IL-17A, IL-2 and IFNγ were analyzed by ELISA. It was observed that the incorporation of the CD137 signaling domain in combination with ICOS did not alter the cytokine profile of Th17 cells redirected with a CAR containing only the ICOS costimulatory domain (FIG. 9B).

Figure 10A:
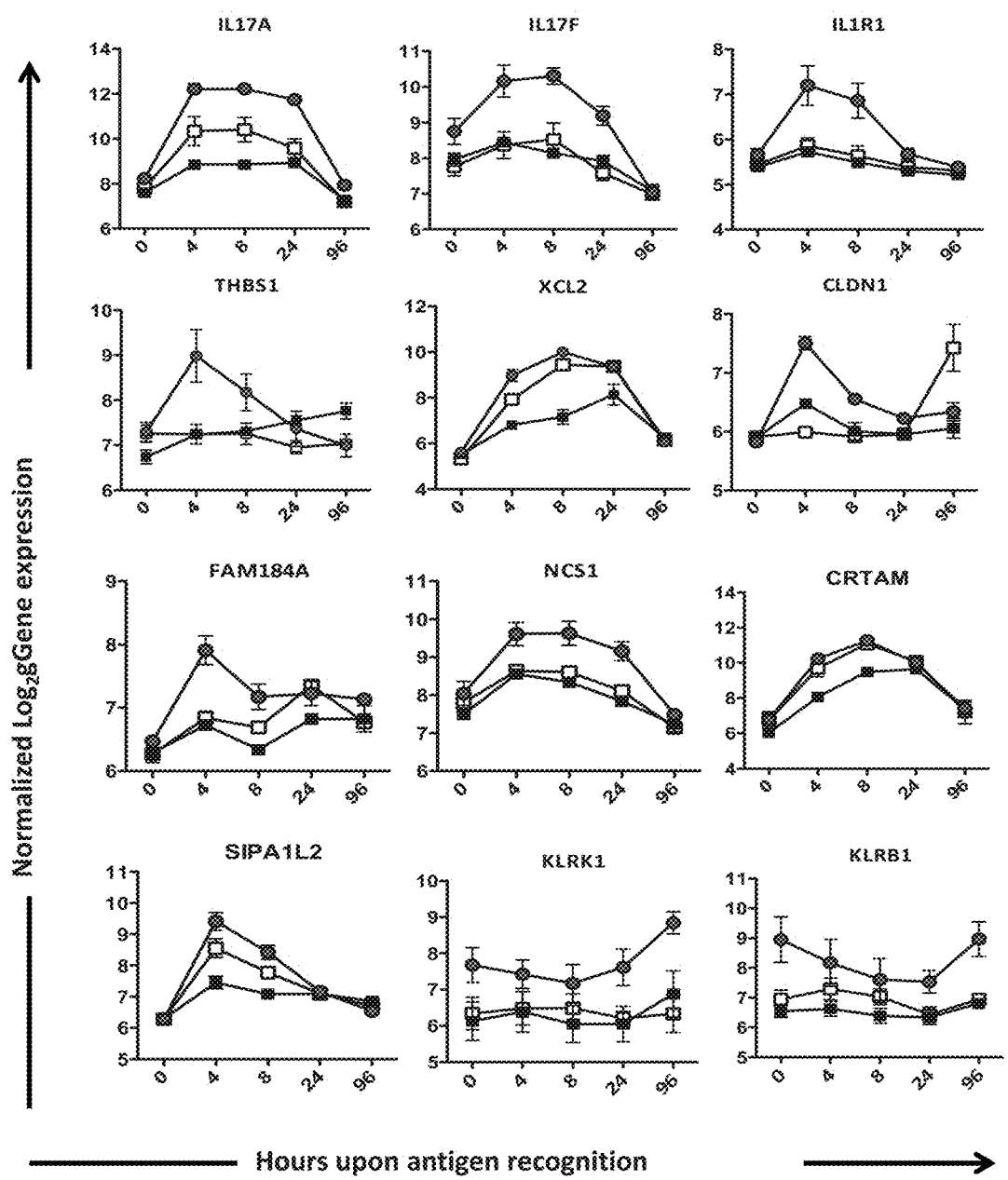
FIGS. 10A through 10C, is a series of images demonstrating that $T_H17$ cells redirected with ICOSz showed increased expression of $T_H17$-related genes. Redirected $T_H17$ cells were stimulated with immobilized yeast-derived recombinant Mesothelin. Gene expression levels were determined on day 0 prior to stimulation and 4h, 8h, 24h and 96h upon antigen recognition.
Figure 10B:
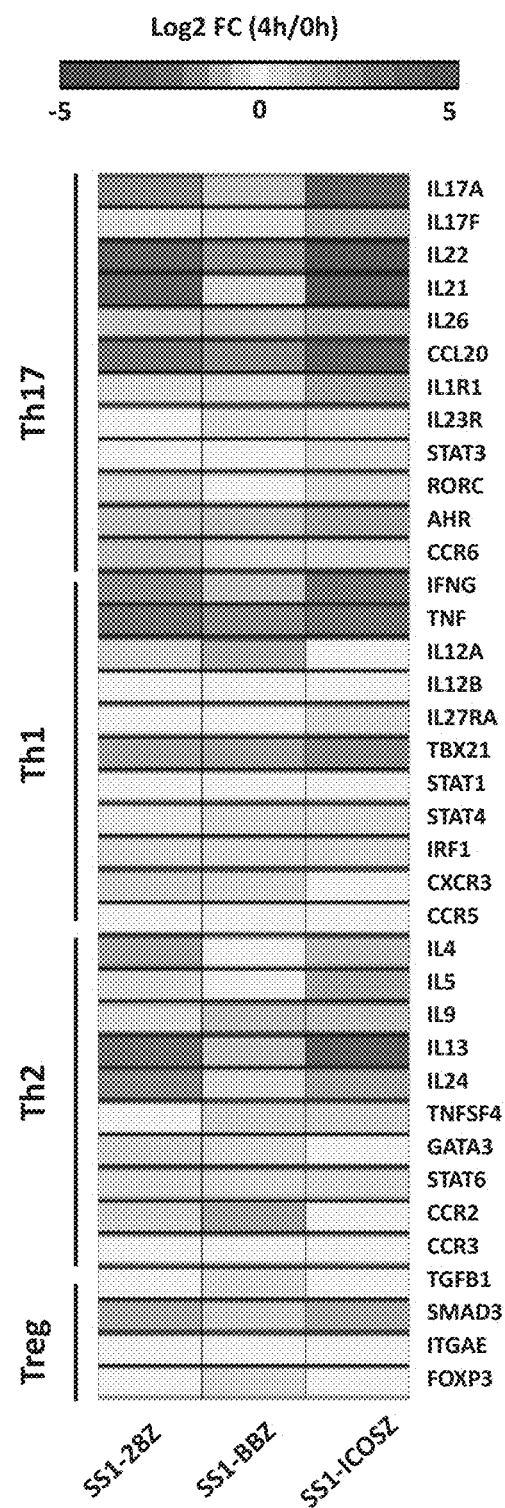
Figure 10C:
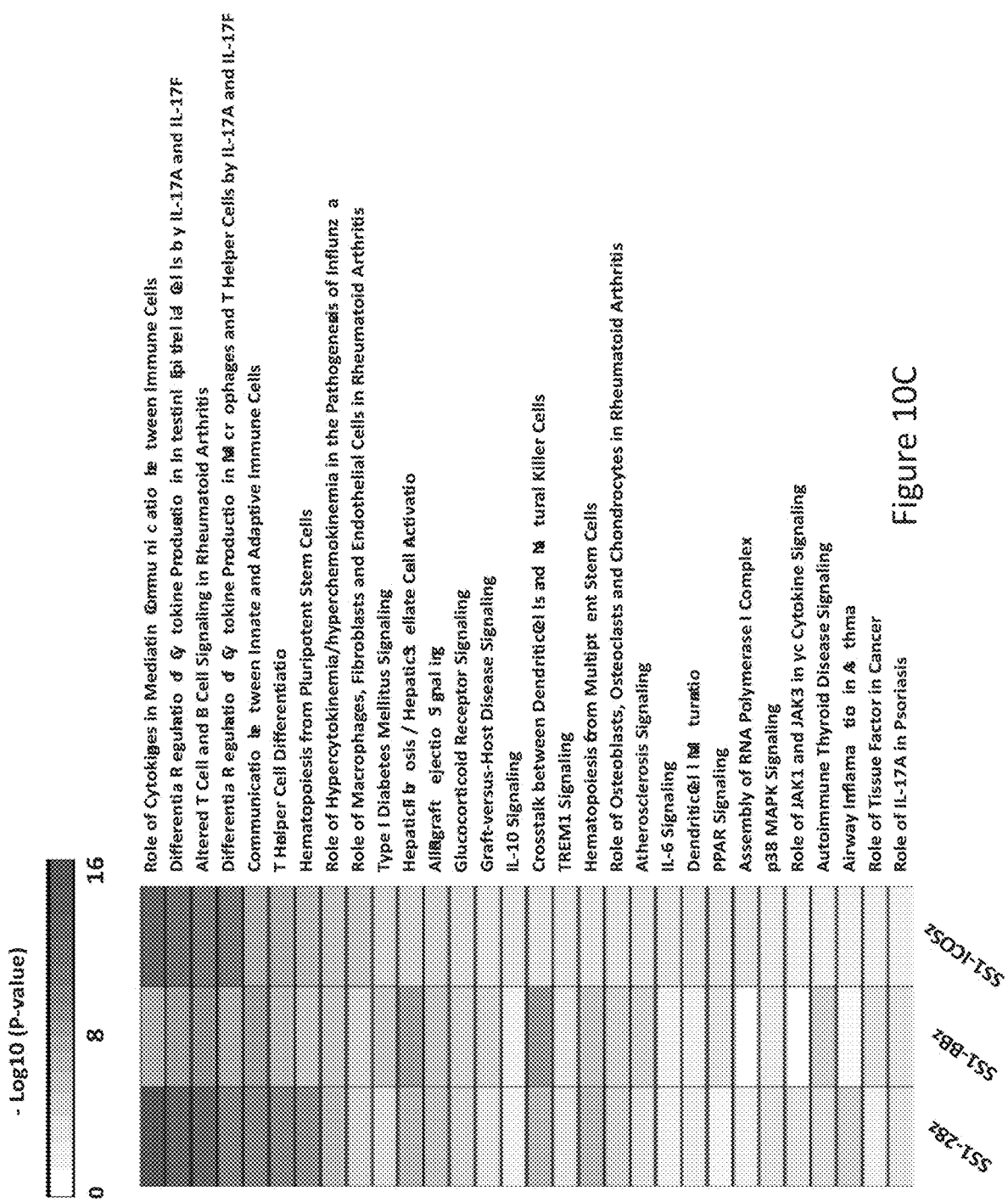

CARs that include both the ICOS and CD137 domains were further evaluated for their ability to drive T cell expansion. Redirected Th17 cells were co-cultured with irradiated APC expressing mesothelin at a 1:1 ratio in the absence of exogenous cytokines. Expansion of Th17 redirected cells was measured in response to mesothelin-specific stimulation. Viable cells were counted by trypan blue exclusion at various time points. It was observed that incorporation of the CD137 signaling domain into ICOS based CAR enhances T cell expansion (FIG. 10A). The phenotype of cells expressing ICOS based CARs that either do or do not contain the CD137 signaling domain were compared. The percentage of CAR$^+$CD45RO$^+$CD4$^+$ cells expressing CCR7 and CD27 was analyzed with flow cytometry at day 0 (before Ag recognition) or 11 days after stimulation. It was observed that incorporation of the CD137 signaling domain into ICOS based CAR directs cells towards a memory phenotype.

It was also observed that different genes were differentially expressed in the ICOSz group compared to the 28z and BBz groups at the different time points. A summary of these genes are listed in Tables 1-8.

TABLE 1

Genes differentially upregulated in $T_H17$ cells redirected with SS1-ICOSz compared to SS1-BBz at 4 hours upon antigen recognition. Gene expression profiling was performed on T cells before activation (day 0) and 4 h upon antigen recognition. Only genes that were differentially upregulated in the ICOSz cells compared with the BBz cells by >2-fold change that had a false discovery rate (FDR) <0.05 are shown. Genes that showed >2-fold change at 4 h compared with 0 h in the SS1-ICOSz group are marked in bold type.

| Gene | Gene Name | GeneBank | p-value | Fold Change (ICOS vs BB) | Fold Change (4 h vs 0 h) |
|---|---|---|---|---|---|
| IL17A | interleukin 17A | NM_002190 | 2.4E−08 | 10.2 | 15.9 |
| CCL20 | chemokine (C-C motif) ligand 20 | NM_004591 | 2.0E−07 | 8.3 | 12.0 |
| IL31 | interleukin 31 | NM_001014336 | 6.0E−04 | 5.8 | 10.1 |
| IL22 | interleukin 22 | NM_020525 | 1.0E−03 | 5.7 | 29.6 |
| CD160 | CD160 molecule | NM_007053 | 8.8E−08 | 5.1 | 5.4 |
| IL10 | interleukin 10 | NM_000572 | 1.8E−06 | 4.7 | 6.8 |
| CRTAM | cytotoxic and regulatory T cell molecule | NM_019604 | 2.4E−04 | 4.5 | 11.0 |
| XCL2 | chemokine (C motif) ligand 2 | NM_003175 | 1.4E−06 | 4.5 | 10.2 |
| SIPA1L2 | signal-induced proliferation-associated 1 like 2 | NM_020808 | 8.9E−09 | 3.9 | 8.8 |
| TGFBR3 | transforming growth factor, beta receptor III | NM_003243 | 1.4E−05 | 3.9 | 1.5 |
| B3GNT5 | UDP-GlcNAc:betaGal beta-1,3-N-acetyl-glucosaminyltransferase 5 | NM_032047 | 1.1E−03 | 3.6 | 13.5 |
| THBS1 | thrombospondin 1 | NM_003246 | 7.1E−05 | 3.4 | 3.2 |
| IL17F | interleukin 17F | NM_052872 | 1.1E−04 | 3.3 | 2.7 |
| MFSD2A | major facilitator superfamily domain containing 2A | NM_001136493 | 1.0E−06 | 3.3 | 5.0 |
| NR4A2 | nuclear receptor subfamily 4, group A, member 2 | NM_006186 | 4.7E−04 | 2.9 | 26.1 |
| KLRB1 | killer cell lectin-like receptor subfamily B, member 1 | NM_002258 | 3.2E−02 | 2.9 | −1.7 |
| TAGAP | T-cell activation RhoGTPase activating protein | NM_054114 | 9.1E−11 | 2.9 | 2.8 |
| IL1R1 | interleukin 1 receptor, type I | NM_000877 | 5.2E−06 | 2.8 | 2.9 |
| ADAM12 | ADAM metallopeptidase domain 12 | NM_003474 | 3.8E−02 | 2.8 | 1.1 |
| SNORD20 | small nucleolar RNA | NR_002908 | 3.7E−04 | 2.7 | 2.7 |

TABLE 1-continued

Genes differentially upregulated in $T_H17$ cells redirected with SS1-ICOSz compared to SS1-BBz at 4 hours upon antigen recognition. Gene expression profiling was performed on T cells before activation (day 0) and 4 h upon antigen recognition. Only genes that were differentially upregulated in the ICOSz cells compared with the BBz cells by >2-fold change that had a false discovery rate (FDR) <0.05 are shown. Genes that showed >2-fold change at 4 h compared with 0 h in the SS1-ICOSz group are marked in bold type.

| Gene | Gene Name | GeneBank | p-value | Fold Change (ICOS vs BB) | Fold Change (4 h vs 0 h) |
|---|---|---|---|---|---|
| SLC16A14 | solute carrier family 16, member 14 (monocarboxylic acid transporter 14) | NM_152527 | 6.5E−05 | 2.7 | 2.4 |
| FASLG | Fas ligand (TNF superfamily, member 6) | NM_000639 | 1.2E−07 | 2.7 | 10.2 |
| CDC42EP3 | CDC42 effector protein (Rho GTPase binding) 3 | NM_006449 | 2.3E−05 | 2.7 | 1.8 |
| GLDC | glycine dehydrogenase (decarboxylating) | NM_000170 | 7.5E−03 | 2.6 | 3.1 |
| PHEX | phosphate regulating endopeptidase homolog, X-linked | NM_000444 | 4.7E−04 | 2.6 | 3.8 |
| PTGIS | prostaglandin 12 (prostacyclin) synthase | NM_000961 | 7.2E−03 | 2.6 | 4.1 |
| IL2 | interleukin 2 | NM_000586 | 2.5E−03 | 2.6 | 34.6 |
| SHC4 | SHC (Src homology 2 domain containing) family, member 4 | NM_203349 | 2.2E−03 | 2.5 | 11.7 |
| ARHGAP42 | Rho GTPase activating protein 42 | NM_152432 | 2.1E−03 | 2.5 | 2.5 |
| IRF8 | interferon regulatory factor 8 | NM_002163 | 4.5E−04 | 2.5 | 22.7 |
| IL8 | interleukin 8 | NM_000584 | 8.8E−04 | 2.4 | 9.9 |
| MGAT5 | mannosyl (alpha-1,6-)-glycoprotein beta-1,6-N-acetyl-glucosaminyltransferase | NM_002410 | 3.7E−06 | 2.4 | 1.2 |
| AMIGO2 | adhesion molecule with Ig-like domain 2 | NM_001143668 | 5.6E−06 | 2.4 | 2.1 |
| HRH4 | histamine receptor H4 | NM_021624 | 9.8E−03 | 2.4 | 1.3 |
| KCNK5 | potassium channel, subfamily K, member 5 | NM_003740 | 2.5E−09 | 2.3 | 4.2 |
| ZC3H12C | zinc finger CCCH-type containing 12C | NM_033390 | 1.2E−03 | 2.3 | 4.7 |
| PAM | peptidylglycine alpha-amidating monooxygenase | NM_000919 | 7.2E−07 | 2.3 | 2.8 |
| ZEB2 | zinc finger E-box binding homeobox 2 | NM_014795 | 1.6E−04 | 2.3 | 3.4 |
| VCL | vinculin | NM_014000 | 2.6E−04 | 2.3 | 1.7 |
| FAM184A | family with sequence similarity 184, member A | NM_024581 | 2.6E−05 | 2.3 | 2.7 |
| TMEM2 | transmembrane protein 2 | NM_013390 | 3.7E−06 | 2.2 | 2.7 |
| NIPA1 | non imprinted in Prader-Willi/Angelman syndrome 1 | NM_144599 | 5.6E−05 | 2.2 | 4.4 |
| NCEH1 | neutral cholesterol ester hydrolase 1 | NM_001146276 | 8.6E−06 | 2.2 | 3.0 |
| OTUD1 | OTU domain containing 1 | NM_001145373 | 3.1E−04 | 2.2 | 2.8 |
| KBTBD8 | kelch repeat and BTB (POZ) domain containing 8 | NM_032505 | 2.5E−05 | 2.2 | 4.7 |
| CXCR6 | chemokine (C-X-C motif) receptor 6 | NM_006564 | 4.2E−02 | 2.2 | −1.2 |
| NKG7 | natural killer cell group 7 sequence | NM_005601 | 5.7E−04 | 2.2 | 1.2 |
| XCL1 | chemokine (C motif) ligand 1 | NM_002995 | 2.3E−03 | 2.2 | 4.2 |
| NR4A3 | nuclear receptor subfamily 4, group A, member 3 | NM_006981 | 3.8E−04 | 2.1 | 15.8 |
| TNFSF9 | tumor necrosis factor (ligand) superfamily, member 9 | NM_003811 | 1.0E−02 | 2.1 | 3.8 |
| CCNYL1 | cyclin Y-like 1 | NM_001142300 | 2.9E−05 | 2.1 | 2.8 |
| UBASH3B | ubiquitin associated and SH3 domain containing B | NM_032873 | 1.3E−05 | 2.1 | 1.4 |
| NFKBID | nuclear factor of kappa light polypeptide gene enhancer in B-cells inhibitor, delta | NM_139239 | 6.3E−05 | 2.1 | 5.4 |
| TBL1X | transducin (beta)-like 1X-linked | NM_005647 | 1.1E−06 | 2.1 | 1.5 |
| AHI1 | transducin (beta)-like 1X-linked | NM_001134831 | 1.0E−06 | 2.1 | 2.7 |
| PLEK | pleckstrin | NM_002664 | 1.6E−02 | 2.1 | 2.0 |
| EVI2A | ecotropic viral integration site 2A | NM_001003927 | 7.4E−06 | 2.1 | 1.5 |
| CCL4 | chemokine (C-C motif) ligand 4 | NM_002984 | 4.5E−02 | 2.1 | 10.1 |

TABLE 1-continued

Genes differentially upregulated in $T_H17$ cells redirected with SS1-ICOSz compared to SS1-BBz at 4 hours upon antigen recognition. Gene expression profiling was performed on T cells before activation (day 0) and 4 h upon antigen recognition. Only genes that were differentially upregulated in the ICOSz cells compared with the BBz cells by >2-fold change that had a false discovery rate (FDR) <0.05 are shown. Genes that showed >2-fold change at 4 h compared with 0 h in the SS1-ICOSz group are marked in bold type.

| Gene | Gene Name | GeneBank | p-value | Fold Change (ICOS vs BB) | Fold Change (4 h vs 0 h) |
|---|---|---|---|---|---|
| NCS1 | neuronal calcium sensor 1 | NM_014286 | 1.9E−03 | 2.1 | 3.0 |
| ANK1 | ankyrin 1, erythrocytic | NM_020476 | 9.6E−04 | 2.1 | 1.8 |
| CD40LG | CD40 ligand | NM_000074 | 2.4E−05 | 2.1 | 5.4 |
| RILPL2 | Rab interacting lysosomal protein-like 2 | NM_145058 | 1.6E−06 | 2.1 | 2.5 |
| SLAMF6 | SLAM family member 6 | NM_001184714 | 9.6E−05 | 2.1 | 1.1 |
| CRIM1 | cysteine rich transmembrane BMP regulator 1 (chordin-like) | NM_016441 | 1.2E−03 | 2.1 | 4.4 |
| SLC4A7 | solute carrier family 4, sodium bicarbonate cotransporter, member 7 | NM_003615 | 1.2E−04 | 2.1 | 1.4 |
| VAV3 | vav 3 guanine nucleotide exchange factor | NM_006113 | 7.8E−04 | 2.1 | 1.6 |
| KLRK1 | killer cell lectin-like receptor subfamily K, member 1 | NM_007360 | 6.5E−03 | 2.1 | −1.2 |
| CD200 | CD200 molecule | NM_001004196 | 1.0E−04 | 2.1 | 21.1 |
| PIGV | phosphatidylinositol glycan anchor biosynthesis, class V | NM_017837 | 2.7E−05 | 2.1 | 1.8 |
| IL18RAP | interleukin 18 receptor accessory protein | NM_003853 | 1.9E−02 | 2.1 | 5.3 |
| ZBTB32 | zinc finger and BTB domain containing 32 | NM_014383 | 1.6E−03 | 2.0 | 4.4 |
| CLDN1 | claudin 1 | NM_021101 | 1.5E−04 | 2.0 | 3.2 |
| IL24 | interleukin 24 | NM_006850 | 4.6E−03 | 2.0 | 2.5 |
| GPR18 | G protein-coupled receptor 18 | NM_005292 | 4.1E−05 | 2.0 | 1.5 |
| KLHL8 | kelch-like 8 (Drosophila) | NM_020803 | 8.5E−06 | 2.0 | 2.6 |
| ITGA6 | integrin, alpha 6 | NM_000210 | 5.4E−04 | 2.0 | −1.1 |
| TIGIT | T cell immunoreceptor with Ig and ITIM domains | NM_173799 | 1.9E−03 | 2.0 | 1.1 |

TABLE 2

Genes differentially upregulated in $T_H17$ cells redirected with SS1-ICOSz compared to SS1-28z at 4 hours upon antigen recognition. Gene expression profiling was performed on T cells before activation (day 0) and 4 h upon antigen recognition. Only genes that were differentially upregulated in the ICOSz cells compared with the 28z cells by >2-fold change that had a false discovery rate (FDR) <0.05 are shown. Genes that showed >2-fold change at 4 h compared with 0 h in the SS1-ICOSz group are marked in bold type.

| Gene | Gene Name | GeneBank | p-value | Fold Change (ICOS vs BB) | Fold Change (4 h vs 0 h) |
|---|---|---|---|---|---|
| IL17A | interleukin 17A | NM_002190 | 2.3E−03 | 3.7 | 15.9 |
| IL17F | interleukin 17F | NM_052872 | 1.4E−03 | 3.5 | 2.7 |
| THBS1 | thrombospondin 1 | NM_003246 | 1.4E−03 | 3.3 | 3.2 |
| TNIP3 | TNFAIP3 interacting protein 3 | NM_024873 | 2.4E−02 | 3.1 | 8.6 |
| CLDN1 | claudin 1 | NM_021101 | 2.4E−05 | 2.9 | 3.2 |
| CCL20 | chemokine (C-C motif) ligand 20 | NM_004591 | 3.9E−02 | 2.5 | 12.0 |
| IL1R1 | interleukin 1 receptor, type I | NM_000877 | 6.2E−04 | 2.5 | 2.9 |
| PGM2L1 | phosphoglucomutase 2-like 1 | NM_173582 | 1.9E−03 | 2.4 | −1.1 |
| SCML1 | sex comb on midleg-like 1 (Drosophila) | NM_001037540 | 2.0E−02 | 2.4 | 1.4 |
| HOOK1 | hook homolog 1 (Drosophila) | NM_015888 | 1.2E−03 | 2.3 | 1.9 |
| ZNF485 | zinc finger protein 485 | NM_145312 | 6.2E−04 | 2.3 | 2.4 |
| VSIG1 | V-set and immunoglobulin domain containing 1 | NM_001170553 | 4.7E−02 | 2.2 | −3.9 |
| NIPAL1 | NIPA-like domain containing 1 | NM_207330 | 7.4E−04 | 2.2 | 3.5 |
| FAM184A | family with sequence similarity 184, member A | NM_024581 | 1.8E−03 | 2.1 | 2.7 |
| COL6A3 | collagen, type VI, alpha 3 | NM_004369 | 2.4E−03 | 2.1 | 3.4 |

TABLE 2-continued

Genes differentially upregulated in $T_H17$ cells redirected with SS1-ICOSz compared to SS1-28z at 4 hours upon antigen recognition. Gene expression profiling was performed on T cells before activation (day 0) and 4 h upon antigen recognition. Only genes that were differentially upregulated in the ICOSz cells compared with the 28z cells by >2-fold change that had a false discovery rate (FDR) <0.05 are shown. Genes that showed >2-fold change at 4 h compared with 0 h in the SS1-ICOSz group are marked in bold type.

| Gene | Gene Name | GeneBank | p-value | Fold Change (ICOS vs BB) | Fold Change (4 h vs 0 h) |
|---|---|---|---|---|---|
| XCL2 | chemokine (C motif) ligand 2 | NM_003175 | 4.6E−02 | 2.1 | 10.2 |
| ITGA6 | integrin, alpha 6 | NM_000210 | 6.0E−03 | 2.1 | −1.1 |

TABLE 3

Genes differentially upregulated in $T_H17$ cells redirected with SS1-ICOSz compared to SS1-BBz at 8 hours upon antigen recognition. Gene expression profiling was performed on T cells before activation (day 0) and 8 h upon antigen recognition. Only genes that were differentially upregulated in the ICOSz cells compared with the BBz cells by >2-fold change that had a false discovery rate (FDR) <0.05 are shown. Genes that showed >2-fold change at 8 h compared with 0 h in the SS1-ICOSz group are marked in bold type.

| Gene | Gene Name | GeneBank | p-value | Fold Change (ICOS vs BB) | Fold Change (4 h vs 0 h) |
|---|---|---|---|---|---|
| IL17A | interleukin 17A | NM_002190 | 1.4E−08 | 10.3 | 15.9 |
| CD160 | CD160 molecule | NM_007053 | 9.4E−10 | 7.6 | 8.8 |
| CCL20 | chemokine (C-C motif) ligand 20 | NM_004591 | 4.7E−07 | 7.2 | 10.7 |
| XCL2 | chemokine (C motif) ligand 2 | NM_003175 | 8.4E−09 | 7.2 | 20.9 |
| IL10 | interleukin 10 | NM_000572 | 5.2E−08 | 6.5 | 9.3 |
| B3GNT5 | UDP-GlcNAc:betaGal beta-1,3-N-acetylglucosaminyltransferase | NM_032047 | 7.0E−05 | 5.1 | 10.4 |
| IL22 | interleukin 22 | NM_020525 | 2.8E−03 | 5.0 | 26.5 |
| IL31 | interleukin 31 | NM_001014336 | 3.3E−03 | 4.6 | 8.3 |
| IL17F | interleukin 17F | NM_052872 | 4.2E−06 | 4.5 | 2.9 |
| TGFBR3 | transforming growth factor, beta receptor III | NM_003243 | 2.8E−05 | 3.6 | 1.6 |
| CRTAM | cytotoxic and regulatory T cell molecule | NM_019604 | 2.7E−03 | 3.4 | 22.4 |
| ADAM12 | ADAM metallopeptidase domain 12 | NM_003474 | 1.6E−02 | 3.3 | 1.2 |
| NKG7 | natural killer cell group 7 sequence | NM_005601 | 4.9E−06 | 3.0 | 1.7 |
| FAM102B | family with sequence similarity 102, member B | NM_001010883 | 6.0E−05 | 2.8 | 1.3 |
| SLC16A14 | solute carrier family 16, member 14 (monocarboxylic acid transporter 14) | NM_152527 | 5.6E−05 | 2.7 | 2.7 |
| UBASH3B | ubiquitin associated and SH3 domain containing B | NM_032873 | 1.3E−07 | 2.7 | 2.1 |
| IL1R1 | interleukin 1 receptor, type I | NM_000877 | 1.4E−05 | 2.6 | 2.3 |
| IL24 | interleukin 24 | NM_006850 | 3.5E−04 | 2.5 | 3.6 |
| SIPA1L2 | signal-induced proliferation-associated 1 like 2 | NM_020808 | 4.7E−06 | 2.5 | 4.4 |
| TAGAP | T-cell activation RhoGTPase activating protein | NM_054114 | 9.7E−10 | 2.5 | 2.9 |
| GPR18 | G protein-coupled receptor 18 | NM_005292 | 8.7E−07 | 2.5 | 2.0 |
| PAM | peptidylglycine alpha-amidating monooxygenase | NM_000919 | 1.9E−07 | 2.5 | 3.6 |
| IL18RAP | interleukin 18 receptor accessory protein | NM_003853 | 4.1E−03 | 2.5 | 4.3 |
| NCS1 | neuronal calcium sensor | NM_014286 | 2.6E−04 | 2.4 | 3.0 |
| MFSD2A | major facilitator superfamily domain containing 2A | NM_001136493 | 6.4E−05 | 2.4 | 5.5 |
| MGAT5 | mannosyl (alpha-1,6-)-glycoprotein beta-1,6-N-acetyl-glucosaminyltransferase | NM_002410 | 4.2E−06 | 2.4 | −1.0 |

TABLE 3-continued

Genes differentially upregulated in $T_H17$ cells redirected with SS1-ICOSz compared to SS1-BBz at 8 hours upon antigen recognition. Gene expression profiling was performed on T cells before activation (day 0) and 8 h upon antigen recognition. Only genes that were differentially upregulated in the ICOSz cells compared with the BBz cells by >2-fold change that had a false discovery rate (FDR) <0.05 are shown. Genes that showed >2-fold change at 8 h compared with 0 h in the SS1-ICOSz group are marked in bold type.

| Gene | Gene Name | GeneBank | p-value | Fold Change (ICOS vs BB) | Fold Change (4 h vs 0 h) |
|---|---|---|---|---|---|
| CDC42EP3 | CDC42 effector protein (Rho GTPase binding) 3 | NM_006449 | 1.1E−04 | 2.4 | 1.2 |
| TIGIT | T cell immunoreceptor with Ig and ITIM domains | NM_173799 | 2.4E−04 | 2.3 | 1.4 |
| XCL1 | chemokine (C motif) ligand 1 | NM_002995 | 1.2E−03 | 2.3 | 6.1 |
| IL8 | interleukin 8 | NM_000584 | 2.6E−03 | 2.3 | 5.5 |
| FASLG | Fas ligand (TNF superfamily, member 6) | NM_000639 | 2.6E−06 | 2.2 | 9.4 |
| GLDC | glycine dehydrogenase (decarboxylating) | NM_000170 | 3.9E−02 | 2.2 | 2.5 |
| OTUD1 | OTU domain containing 1 | NM_001145373 | 2.7E−04 | 2.2 | 1.9 |
| IRF8 | interferon regulatory factor 8 | NM_002163 | 2.6E−03 | 2.2 | 22.0 |
| KLRK1 | killer cell lectin-like receptor subfamily K, member 1 | NM_007360 | 4.0E−03 | 2.2 | −1.4 |
| ANK1 | ankyrin 1, erythrocytic | NM_020476 | 6.6E−04 | 2.2 | 2.3 |
| HRH4 | histamine receptor H4 | NM_021624 | 3.0E−02 | 2.1 | 1.0 |
| PLEK | pleckstrin | NM_002664 | 1.7E−02 | 2.1 | 2.3 |
| TBL1X | transducin (beta)-like 1X-linked | NM_005647 | 7.4E−07 | 2.1 | 1.4 |
| NCR3 | natural cytotoxicity triggering receptor 3 | NM_001145466 | 6.2E−04 | 2.1 | −1.3 |
| NR4A3 | nuclear receptor subfamily 4, group A, member 3 | NM_006981 | 5.4E−04 | 2.1 | 13.5 |
| RIN3 | Ras and Rab interactor 3 | NM_024832 | 1.6E−05 | 2.1 | 1.2 |
| CFH | complement factor H | NM_000186 | 1.9E−02 | 2.1 | 1.0 |
| AMIGO2 | adhesion molecule with Ig-like domain 2 | NM_001143668 | 7.1E−05 | 2.1 | 1.6 |
| CD40LG | CD40 ligand | NM_000074 | 2.7E−05 | 2.1 | 4.0 |
| IKZF3 | IKAROS family zinc finger 3 (Aiolos) | NM_012481 | 3.6E−06 | 2.0 | 1.5 |
| FABP5 | fatty acid binding protein 5 (psoriasis-associated) | NM_001444 | 2.3E−04 | 2.0 | 6.0 |
| CD72 | CD72 molecule | NM_001782 | 7.1E−06 | 2.0 | 2.3 |
| FABP5 | fatty acid binding protein 5 (psoriasis-associated) | NM_001444 | 1.9E−04 | 2.0 | 5.8 |
| PHEX | phosphate regulating endopeptidase homolog, X-linked | NM_000444 | 1.1E−02 | 2.0 | 7.9 |
| HECTD2 | HECT domain containing 2 | NM_182765 | 7.1E−06 | 2.0 | 4.4 |
| DACT1 | dapper, antagonist of beta-catenin, homolog 1 (Xenopus laevis) | NM_016651 | 1.9E−02 | 2.0 | 2.4 |
| TMEM2 | transmembrane protein 2 | NM_013390 | 2.4E−05 | 2.0 | 2.1 |
| VCL | vinculin | NM_014000 | 1.8E−03 | 2.0 | 1.9 |
| RAB30 | RAB30, member RAS oncogene family | NM_014488 | 9.4E−05 | 2.0 | 1.6 |
| FAM113B | family with sequence similarity 113, member B | BC008360 | 2.7E−06 | 2.0 | 1.1 |
| HOMER2 | homer homolog 2 (Drosophila) | NM_199330 | 9.0E−03 | 2.0 | 1.5 |

TABLE 4

Genes differentially upregulated in T$_H$17 cells redirected with SS1-ICOSz compared to SS1-28z at 8 hours upon antigen recognition. Gene expression profiling was performed on T cells before activation (day 0) and 8 h upon antigen recognition. Only genes that were differentially upregulated in the ICOSz cells compared with the 28z cells by >2-fold change that had a false discovery rate (FDR) <0.05 are shown. Genes that showed >2-fold change at 8 h compared with 0 h in the SS1-ICOSz group are marked in bold type.

| Gene | Gene Name | GeneBank | p-value | Fold Change (ICOS vs 28) | Fold Change (4 h vs 0 h) |
| --- | --- | --- | --- | --- | --- |
| IL17A | interleukin 17A | NM_002190 | 5.4E−03 | 3.5 | 15.9 |
| IL17F | interleukin 17F | NM_052872 | 2.0E−03 | 3.4 | 2.9 |
| TNIP3 | TNFAIP3 interacting protein 3 | NM_024873 | 5.9E−02 | 2.9 | 5.6 |
| FAM49A | family with sequence similarity 49, member A | NM_030797 | 1.4E−04 | 2.7 | 4.2 |
| CXCL13 | chemokine (C—X—C motif) ligand 13 | NM_006419 | 7.9E−02 | 2.4 | 1.7 |
| IL1R1 | interleukin 1 receptor, type I | NM_000877 | 2.0E−03 | 2.3 | 2.3 |
| VSIG1 | V-set and immunoglobulin domain containing 1 | NM_001170553 | 6.3E−02 | 2.3 | −7.0 |
| NCS1 | neuronal calcium sensor 1 | NM_014286 | 3.6E−02 | 2.0 | 3.0 |

TABLE 5

Genes differentially upregulated in T$_H$17 cells redirected with SS1-ICOSz compared to SS1-BBz at 24 hours upon antigen recognition. Gene expression profiling was performed on T cells before activation (day 0) and 24 h upon antigen recognition. Only genes that were differentially upregulated in the ICOSz cells compared with the BBz cells by >2-fold change that had a false discovery rate (FDR) <0.05 are shown. Genes that showed >2-fold change at 24 h compared with 0 h in the SS1-ICOSz group are marked in bold type.

| Gene | Gene Name | GeneBank | p-value | Fold Change (ICOS vs BB) | Fold Change (24 h vs 0 h) |
| --- | --- | --- | --- | --- | --- |
| IL17A | interleukin 17A | NM_002190 | 5.3E−07 | 7.0 | 11.4 |
| B3GNT5 | UDP-GlcNAc:betaGal beta-1,3-N-acetylglucosaminyltransferase 5 | NM_032047 | 3.7E−05 | 5.8 | 9.2 |
| TGFBR3 | transforming growth factor, beta receptor III | NM_003243 | 2.1E−06 | 4.7 | 1.6 |
| IL10 | interleukin 10 | NM_000572 | 3.2E−06 | 4.5 | 7.0 |
| C1orf150 | chromosome 1 open reading frame 150 | ENST00000366488 | 1.2E−10 | 4.3 | 4.9 |
| CCL20 | chemokine (C-C motif) ligand 20 | NM_004591 | 1.2E−03 | 3.2 | 5.3 |
| TIGIT | T cell immunoreceptor with Ig and ITIM domains | NM_173799 | 5.6E−06 | 3.1 | 2.0 |
| ACTG2 | actin, gamma 2, smooth muscle, enteric | NM_001615 | 1.5E−07 | 3.0 | 3.3 |
| KLRK1 | killer cell lectin-like receptor subfamily K, member 1 | NM_007360 | 1.3E−04 | 3.0 | −1.0 |
| DKFZp686O24166 | hypothetical protein DKFZp686O24166 | NR_026750 | 7.4E−06 | 2.8 | 3.5 |
| RAB38 | RAB38, member RAS oncogene family | NM_022337 | 1.2E−05 | 2.7 | 2.8 |
| PLK2 | polo-like kinase 2 | NM_006622 | 9.1E−05 | 2.6 | 6.3 |
| NCS1 | neuronal calcium sensor 1 | NM_014286 | 2.4E−04 | 2.5 | 2.2 |
| UBASH3B | ubiquitin associated and SH3 domain containing B | NM_032873 | 8.7E−07 | 2.5 | 2.2 |
| IL22 | interleukin 22 | NM_020525 | 1.4E−01 | 2.5 | 9.4 |
| FAM102B | family with sequence similarity 102, member B | NM_001010883 | 4.6E−04 | 2.5 | 1.0 |
| SNORD12C | small nucleolar RNA, C/D box 12C | NR_002433 | 8.6E−06 | 2.4 | 3.7 |

TABLE 5-continued

Genes differentially upregulated in T$_H$17 cells redirected with SS1-ICOSz compared to SS1-BBz at 24 hours upon antigen recognition. Gene expression profiling was performed on T cells before activation (day 0) and 24 h upon antigen recognition. Only genes that were differentially upregulated in the ICOSz cells compared with the BBz cells by >2-fold change that had a false discovery rate (FDR) <0.05 are shown. Genes that showed >2-fold change at 24 h compared with 0 h in the SS1-ICOSz group are marked in bold type.

| Gene | Gene Name | GeneBank | p-value | Fold Change (ICOS vs BB) | Fold Change (24 h vs 0 h) |
|---|---|---|---|---|---|
| NKG7 | natural killer cell group 7 sequence | NM_005601 | 1.7E−04 | 2.4 | 2.2 |
| IL17F | interleukin 17F | NM_052872 | 4.3E−03 | 2.4 | 1.4 |
| MYO1E | myosin IE | NM_004998 | 9.9E−05 | 2.4 | 3.8 |
| DTHD1 | death domain containing 1 | NM_001136536 | 4.8E−04 | 2.4 | 1.7 |
| NCR3 | natural cytotoxicity triggering receptor 3 | NM_001145466 | 1.5E−04 | 2.4 | 1.2 |
| IL18RAP | interleukin 18 receptor accessory protein | NM_003853 | 7.1E−03 | 2.4 | 3.6 |
| CTSL1 | cathepsin L1 | NM_001912 | 5.1E−04 | 2.3 | −2.8 |
| XCL2 | chemokine (C motif) ligand 2 | NM_003175 | 3.2E−03 | 2.3 | 13.3 |
| SNORD50B | small nucleolar RNA, C/D box 50B | NR_003044 | 3.7E−05 | 2.3 | 2.8 |
| ATP8B4 | ATPase, class I, type 8B, member 4 | NM_024837 | 5.5E−03 | 2.3 | 2.5 |
| CFH | complement factor H | NM_000186 | 1.1E−02 | 2.2 | 1.2 |
| CD160 | CD160 molecule | NM_007053 | 2.6E−03 | 2.2 | 2.2 |
| PMP22 | peripheral myelin protein 22 | NM_000304 | 5.3E−02 | 2.2 | 5.9 |
| QPCT | glutaminyl-peptide cyclotransferase | NM_012413 | 4.6E−05 | 2.2 | 2.5 |
| CCR4 | chemokine (C-C motif) receptor 4 | NM_005508 | 4.0E−05 | 2.2 | −1.2 |
| KLHL11 | kelch-like 11 (Drosophila) | NM_018143 | 1.4E−08 | 2.1 | 3.1 |
| TBL1X | transducin (beta)-like 1X-linked | NM_005647 | 1.0E−06 | 2.1 | −1.1 |
| LAX1 | lymphocyte transmembrane adaptor 1 | NM_017773 | 4.6E−06 | 2.1 | −1.0 |
| ASB2 | ankyrin repeat and SOCS box-containing 2 | NM_016150 | 2.6E−02 | 2.1 | −1.3 |
| SNORD77 | small nucleolar RNA, C/D box 77 | NR_003943 | 6.3E−03 | 2.1 | 4.4 |
| IL8 | interleukin 8 | NM_000584 | 8.7E−03 | 2.1 | 2.2 |
| IL18R1 | interleukin 18 receptor 1 | NM_003855 | 5.3E−03 | 2.0 | 4.0 |
| TMEM2 | transmembrane protein 2 | NM_013390 | 2.6E−05 | 2.0 | 1.8 |
| PIK3CG | phosphoinositide-3-kinase, catalytic, gamma polypeptide | NM_002649 | 1.1E−08 | 2.0 | −1.0 |
| C7orf68 | chromosome 7 open reading frame 68 | NM_013332 | 1.6E−03 | 2.0 | 2.9 |
| CTLA4 | cytotoxic T-lymphocyte-associated protein 4 | NM_005214 | 1.9E−04 | 2.0 | 1.3 |
| LGMN | legumain | NM_005606 | 6.2E−03 | 2.0 | −4.0 |
| TMEM99 | transmembrane protein 99 | NM_145274 | 5.4E−07 | 2.0 | 3.0 |

TABLE 6

Genes differentially upregulated in T$_H$17 cells redirected with SS1-ICOSz compared to SS1-28z at 24 hours upon antigen recognition. Gene expression profiling was performed on T cells before activation (day 0) and 24 h upon antigen recognition. Only genes that were differentially upregulated in the ICOSz cells compared with the 28z cells by >2-fold change that had a false discovery rate (FDR) <0.05 are shown. Genes that showed >2-fold change at 24 h compared with 0 h in the SS1-ICOSz group are marked in bold type.

| Gene | Gene Name | GeneBank | p-value | Fold Change (ICOS vs 28) | Fold Change (4 h vs 0 h) |
|---|---|---|---|---|---|
| IL17A | interleukin 17A | NM_002190 | 8.4E−04 | 4.5 | 15.9 |
| IL17F | interleukin 17F | NM_052872 | 8.5E−03 | 3.0 | 2.9 |
| C1orf150 | chromosome 1 open reading frame 150 | ENST00000366488 | 2.6E−06 | 2.9 | 1.3 |

TABLE 6-continued

Genes differentially upregulated in T$_H$17 cells redirected with SS1-ICOSz compared to SS1-28z at 24 hours upon antigen recognition. Gene expression profiling was performed on T cells before activation (day 0) and 24 h upon antigen recognition. Only genes that were differentially upregulated in the ICOSz cells compared with the 28z cells by >2-fold change that had a false discovery rate (FDR) <0.05 are shown. Genes that showed >2-fold change at 24 h compared with 0 h in the SS1-ICOSz group are marked in bold type.

| Gene | Gene Name | GeneBank | p-value | Fold Change (ICOS vs 28) | Fold Change (4 h vs 0 h) |
|---|---|---|---|---|---|
| KLRK1 | killer cell lectin-like receptor subfamily K, member 1 | NM_007360 | 9.9E−03 | 2.6 | −1.4 |
| ACTG2 | actin, gamma 2, smooth muscle, enteric | NM_001615 | 5.6E−04 | 2.3 | 1.4 |

TABLE 7

Genes differentially upregulated in T$_H$17 cells redirected with SS1-ICOSz compared to SS1-BBz at 96 hours upon antigen recognition. Gene expression profiling was performed on T cells before activation (day 0) and 96 h upon antigen recognition. Only genes that were differentially upregulated in the ICOSz cells compared with the BBz cells by >2-fold change that had a false discovery rate (FDR) <0.05 are shown. Genes that showed >2-fold change at 96 h compared with 0 h in the SS1-ICOSz group are marked in bold type.

| Gene | Gene Name | GeneBank | p-value | Fold Change (ICOS vs BB) | Fold Change (96 h vs 0 h) |
|---|---|---|---|---|---|
| GPR15 | G protein-coupled receptor 15 | NM_005290 | 5.4E−05 | 5.5 | 1.9 |
| SLAMF7 | SLAM family member 7 | NM_021181 | 1.4E−09 | 5.3 | 2.6 |
| ASB2 | ankyrin repeat and SOCS box-containing 2 | NM_016150 | 2.0E−06 | 5.1 | 1.5 |
| KLRB1 | killer cell lectin-like receptor subfamily B, member 1 | NM_002258 | 2.1E−03 | 4.5 | 1.0 |
| KLRK1 | killer cell lectin-like receptor subfamily K, member 1 | NM_007360 | 3.0E−06 | 3.9 | 2.2 |
| TIGIT | T cell immunoreceptor with Ig and ITIM domains | NM_173799 | 2.3E−07 | 3.8 | 3.0 |
| FGFR1 | fibroblast growth factor receptor 1 | NM_023110 | 2.5E−10 | 3.8 | 3.5 |
| METTL7A | methyltransferase like 7A | NM_014033 | 5.9E−08 | 3.8 | 3.7 |
| CD86 | CD86 molecule | NM_175862 | 1.1E−05 | 3.5 | 2.3 |
| CEP70 | centrosomal protein 70 kDa | NM_024491 | 4.5E−07 | 3.2 | 2.3 |
| HPGD | hydroxyprostaglandin dehydrogenase 15-(NAD) | NM_000860 | 5.7E−03 | 3.1 | 1.8 |
| PYHIN1 | pyrin and HIN domain family, member 1 | NM_152501 | 2.2E−09 | 2.9 | 1.1 |
| F2R | coagulation factor II (thrombin) receptor | NM_001992 | 8.4E−04 | 2.9 | 1.5 |
| RNF125 | ring finger protein 125 | NM_017831 | 4.6E−07 | 2.8 | −1.1 |
| SLCO4C1 | solute carrier organic anion transporter family, member 4C1 | AF119865 | 1.2E−03 | 2.8 | 1.1 |
| RASGRP3 | RAS guanyl releasing protein 3 (calcium and DAG-regulated) | NM_170672 | 8.4E−03 | 2.8 | 1.8 |
| FAIM3 | Fas apoptotic inhibitory molecule 3 | NM_005449 | 1.4E−05 | 2.7 | −1.6 |
| NMT2 | N-myristoyltransferase 2 | NM_004808 | 4.6E−05 | 2.7 | 1.2 |
| CABLES1 | Cdk5 and Abl enzyme substrate 1 | NM_138375 | 4.7E−07 | 2.7 | 2.3 |
| RGS9 | regulator of G-protein signaling 9 | NM_003835 | 2.8E−05 | 2.7 | 1.8 |
| PDLIM1 | PDZ and LIM domain 1 | NM_020992 | 1.1E−03 | 2.7 | 2.5 |
| VNN2 | vanin 2 | NM_004665 | 1.5E−06 | 2.6 | 2.1 |
| CECR1 | cat eye syndrome chromosome region, candidate 1 | NM_017424 | 1.2E−05 | 2.6 | −1.4 |
| VSIG1 | V-set and immunoglobulin domain containing 1 | NM_001170553 | 1.3E−03 | 2.6 | −4.3 |
| P2RX5 | purinergic receptor P2X, ligand-gated ion channel, 5 | NM_002561 | 3.4E−06 | 2.5 | 2.3 |
| SLC12A7 | solute carrier family 12 (potassium/chloride transporters), member 7 | NM_006598 | 2.5E−06 | 2.5 | −1.2 |

TABLE 7-continued

Genes differentially upregulated in T$_H$17 cells redirected with SS1-ICOSz compared to SS1-BBz at 96 hours upon antigen recognition. Gene expression profiling was performed on T cells before activation (day 0) and 96 h upon antigen recognition. Only genes that were differentially upregulated in the ICOSz cells compared with the BBz cells by >2-fold change that had a false discovery rate (FDR) <0.05 are shown. Genes that showed >2-fold change at 96 h compared with 0 h in the SS1-ICOSz group are marked in bold type.

| Gene | Gene Name | GeneBank | p-value | Fold Change (ICOS vs BB) | Fold Change (96 h vs 0 h) |
|---|---|---|---|---|---|
| PION | pigeon homolog (*Drosophila*) | NM_017439 | 1.1E−04 | 2.5 | 1.1 |
| UBASH3B | ubiquitin associated and SH3 domain containing B | NM_032873 | 6.2E−07 | 2.5 | 1.5 |
| LY9 | lymphocyte antigen 9 | NM_002348 | 1.3E−06 | 2.5 | −2.0 |
| DTHD1 | death domain containing 1 | NM_001136536 | 2.0E−04 | 2.4 | 9.2 |
| PTPLAD2 | protein tyrosine phosphatase-like A domain containing 2 | NM_001010915 | 8.9E−08 | 2.4 | 1.1 |
| SUSD1 | sushi domain containing 1 | NM_022486 | 2.3E−09 | 2.4 | −1.5 |
| HSH2D | hematopoietic SH2 domain containing | NM_032855 | 3.5E−04 | 2.4 | 3.2 |
| CD244 | CD244 molecule, natural killer cell receptor 2B4 | NM_016382 | 1.4E−03 | 2.4 | 1.3 |
| SORL1 | sortilin-related receptor, L(DLR class) A repeats-containing | NM_003105 | 2.2E−05 | 2.3 | −1.3 |
| PDP1 | pyruvate dehydrogenase phosphatase catalytic subunit 1 | NM_001161778 | 2.5E−09 | 2.3 | −1.2 |
| TGFBR3 | transforming growth factor, beta receptor III | NM_003243 | 3.7E−03 | 2.3 | −1.2 |
| GALNT3 | UDP-N-acetyl-alpha-D-galactosamine:polypeptide N-acetylgalactosaminyltransferase 3 (GalNAc-T3) | NM_004482 | 5.2E−06 | 2.3 | 2.0 |
| TOX | thymocyte selection-associated high mobility group box | NM_014729 | 2.1E−05 | 2.2 | 1.3 |
| CXCR6 | chemokine (C-X-C motif) receptor 6 | NM_006564 | 3.6E−02 | 2.2 | −1.5 |
| FAR2 | fatty acyl CoA reductase 2 | NM_018099 | 6.2E−06 | 2.2 | −1.2 |
| IL9R | interleukin 9 receptor | NR_024033 | 4.6E−07 | 2.1 | 1.4 |
| DAAM1 | dishevelled associated activator of morphogenesis 1 | NM_014992 | 1.3E−04 | 2.1 | −1.3 |
| RASGRP2 | RAS guanyl releasing protein 2 (calcium and DAG-regulated) | NM_001098671 | 3.9E−08 | 2.1 | −1.8 |
| TCEA3 | transcription elongation factor A (SII), 3 | NM_003196 | 5.3E−04 | 2.1 | 1.9 |
| GIMAP7 | GTPase, IMAP family member 7 | NM_153236 | 3.9E−04 | 2.1 | −1.2 |
| MYO1F | myosin IF | NM_012335 | 9.6E−07 | 2.1 | −1.2 |
| TBL1X | transducin (beta)-like 1X-linked | NM_005647 | 1.3E−06 | 2.1 | −1.4 |
| SLCO3A1 | solute carrier organic anion transporter family, member 3A1 | NM_013272 | 1.7E−06 | 2.1 | −1.9 |
| LZTFL1 | leucine zipper transcription factor-like 1 | NM_020347 | 2.6E−02 | 2.1 | −1.1 |
| LOC283588 | hypothetical LOC283588 | AK095276 | 2.4E−05 | 2.0 | 1.2 |
| HIST1H2AJ | histone cluster 1, H2aj | NM_021066 | 1.4E−02 | 2.0 | −1.0 |
| CCR4 | chemokine (C-C motif) receptor 4 | NM_005508 | 8.0E−05 | 2.0 | −1.7 |
| HIP1 | huntingtin interacting protein 1 | NM_005338 | 6.4E−06 | 2.0 | 1.4 |
| AOAH | acyloxyacyl hydrolase (neutrophil) | NM_001637 | 3.8E−03 | 2.0 | 3.5 |

TABLE 8

Genes differentially upregulated in T$_H$17 cells redirected with SS1-ICOSz compared to SS1-28z at 96 hours upon antigen recognition. Gene expression profiling was performed on T cells before activation (day 0) and 96 h upon antigen recognition. Only genes that were differentially upregulated in the ICOSz cells compared with the 28z cells by >2-fold change that had a false discovery rate (FDR) <0.05 are shown. Genes that showed >2-fold change at 96 h compared with 0 h in the SS1-ICOSz group are marked in bold type.

| Gene | Gene Name | GeneBank | p-value | Fold Change (ICOS vs 28) | Fold Change (96 h vs 0 h) |
|---|---|---|---|---|---|
| KLRK1 | killer cell lectin-like receptor subfamily K, member 1 | NM_007360 | 2.0E−07 | 5.7 | 2.2 |
| KLRB1 | killer cell lectin-like receptor subfamily B, member 1 | NM_002258 | 6.3E−03 | 4.1 | 1.0 |
| VSIG1 | V-set and immunoglobulin domain containing 1 | NM_001170553 | 3.7E−04 | 3.1 | −4.3 |
| PTPN13 | protein tyrosine phosphatase, non-receptor type 13 (APO-1/CD95 (Fas)-associated phosphatase) | NM_080683 | 2.9E−02 | 2.9 | −1.0 |
| DTHD1 | death domain containing 1 | NM_001136536 | 4.0E−05 | 2.9 | 9.2 |
| SLCO4C1 | solute carrier organic anion transporter family, member 4C1 | AF119865 | 2.4E−03 | 2.8 | 1.1 |
| GNG4 | guanine nucleotide binding protein (G protein), gamma 4 | NM_001098721 | 7.4E−05 | 2.6 | 3.3 |
| CEP68 | centrosomal protein 68 kDa | NM_015147 | 1.2E−06 | 2.4 | 1.5 |
| CD244 | CD244 molecule, natural killer cell receptor 2B4 | NM_016382 | 2.0E−03 | 2.4 | 1.3 |
| METTL7A | methyltransferase like 7A | NM_014033 | 1.4E−04 | 2.3 | 3.7 |
| C6orf105 | chromosome 6 open reading frame 105 | NM_001143948 | 1.8E−03 | 2.3 | 2.5 |
| CXCL13 | chemokine (C-X-C motif) ligand 13 | NM_006419 | 1.9E−02 | 2.3 | 2.9 |
| IPCEF1 | interaction protein for cytohesin exchange factors 1 | NM_001130700 | 3.4E−04 | 2.3 | −1.5 |
| TCF7 | transcription factor 7 (T-cell specific, HMG-box) | NM_003202 | 1.2E−03 | 2.3 | −1.3 |
| KLRC1 | killer cell lectin-like receptor subfamily C, member 1 | NM_213658 | 2.8E−03 | 2.3 | 1.9 |
| CHRNA6 | cholinergic receptor, nicotinic, alpha 6 | NM_004198 | 3.2E−04 | 2.3 | 2.4 |
| GPA33 | glycoprotein A33 (transmembrane) | NM_005814 | 8.3E−04 | 2.2 | −1.5 |
| LY9 | lymphocyte antigen 9 | NM_002348 | 2.3E−05 | 2.2 | −2.0 |
| TXNIP | thioredoxin interacting protein | NM_006472 | 3.9E−06 | 2.2 | 1.1 |
| GLIPR1 | GLI pathogenesis-related 1 | NM_006851 | 7.0E−06 | 2.2 | −1.3 |
| FAIM3 | Fas apoptotic inhibitory molecule 3 | NM_005449 | 7.5E−04 | 2.1 | −1.6 |
| CCL20 | chemokine (C-C motif) ligand 20 | NM_004591 | 4.1E−02 | 2.1 | −1.5 |
| TMEM45B | transmembrane protein 45B | NM_138788 | 1.3E−05 | 2.1 | −1.3 |
| GPR155 | G protein-coupled receptor 155 | NM_001033045 | 2.4E−02 | 2.1 | −1.4 |
| GLCCI1 | glucocorticoid induced transcript 1 | NM_138426 | 7.6E−07 | 2.1 | 1.2 |
| ABCB1 | ATP-binding cassette, sub-family B (MDR/TAP), member 1 | NM_000927 | 4.2E−03 | 2.1 | −1.2 |
| IKZF2 | IKAROS family zinc finger 2 (Helios) | NM_016260 | 1.7E−03 | 2.0 | 1.0 |
| SCML4 | sex comb on midleg-like 4 (Drosophila) | NM_198081 | 2.2E−04 | 2.0 | −1.4 |
| PIK3IP1 | phosphoinositide-3-kinase interacting protein 1 | NM_052880 | 6.3E−04 | 2.0 | −2.1 |

Incorporation of the ICOS signaling domain in CAR T cells imparts novel functions compared to CARs encoding CD28 or 4-1BB signaling domains. Studies presented herein indicate that redirection of Th17 cells with a CAR encoding the ICOS intracellular domain is critical for obtaining potent Th17 cells with enhanced function and persistence. Further, the data presented herein demonstrate that inclusion of the ICOS domain reduces the amount of released IL-2, which is preferred because then the CAR does not trigger the proliferation of T regulatory cells. The design of novel ICOS-based CARs has the potential to augment antitumor effects in clinical trials.

The disclosures of each and every patent, patent application, and publication cited herein are hereby incorporated

What is claimed is:

1. A method of providing an anti-tumor immunity in a mammal, the method comprising administering to the mammal an effective amount of a T cell genetically modified to express a CAR, wherein the CAR comprises an antigen binding domain, an ICOS transmembrane domain, and an ICOS intracellular signaling domain, thereby providing an anti-tumor immunity in the mammal, wherein the ICOS transmembrane domain comprises the amino acid sequence of SEQ ID NO: 12, wherein the antigen binding domain binds to a tumor antigen, wherein the T cell is administered intratumorally, and wherein the T cell induces an immune response to a tumor expressing the tumor antigen and/or reduces tumor volume.

2. The method of claim 1, wherein the CAR further comprises a CD3zeta signaling domain.

3. The method of claim 1, wherein the CAR further comprises a costimulatory signaling region comprising the intracellular domain of a costimulatory molecule selected from the group consisting of CD27, CD28, 4-1BB, OX40, CD30, CD40, PD-1, lymphocyte function-associated antigen-1 (LFA-1), CD2, CD7, LIGHT, NKG2C, B7-H3, a ligand that specifically binds with CD83, and any combination thereof.

4. The method of claim 1, wherein the ICOS intracellular signaling domain comprises the amino acid sequence of SEQ ID NO: 13.

5. The method of claim 1, wherein the antigen binding domain comprises an anti-mesothelin antibody or fragment thereof.

6. A method of treating a human with a tumor, the method comprising administering to the human a cell genetically engineered to express a CAR, wherein the CAR comprises an antigen binding domain, an ICOS transmembrane domain, and an ICOS intracellular signaling domain, wherein the cell is selected from the group consisting of a Th17 cell and a Tc17 cell, wherein the ICOS transmembrane domain comprises the amino acid sequence of SEQ ID NO: 12, wherein the antigen binding domain binds to a tumor antigen, wherein the cell is administered intratumorally, and wherein the cell induces an immune response to a tumor expressing the tumor antigen and/or reduces tumor volume.

7. The method of claim 6, wherein the CAR further comprises a CD3zeta signaling domain.

8. The method of claim 6, wherein the CAR further comprises a costimulatory signaling region comprising the intracellular domain of a costimulatory molecule selected from the group consisting of CD27, CD28, 4-1BB, OX40, CD30, CD40, PD-1, lymphocyte function-associated antigen-1 (LFA-1), CD2, CD7, LIGHT, NKG2C, B7-H3, a ligand that specifically binds with CD83, and any combination thereof.

9. The method of claim 6, wherein the ICOS intracellular signaling domain comprises the amino acid sequence of SEQ ID NO: 13.

10. The method of claim 6, wherein the antigen binding domain comprises an anti-mesothelin antibody or fragment thereof.

11. The method of claim 6, wherein the human is resistant to at least one chemotherapeutic agent.

12. The method of claim 1, wherein the antigen is selected from PSMA, c-Met, Glycolipid F77, EGFRvIII, GD-2, NY-ESO-1 and MAGE A3.

13. The method of claim 6, wherein the antigen is selected from PSMA, c-Met, Glycolipid F77, EGFRvIII, GD-2, NY-ESO-1 and MAGE A3.

14. The method of claim 1, wherein the tumor is selected from mesothelioma, pancreatic cancer, ovarian cancer, triple negative breast cancer, non-small cell lung cancer, prostate cancer and glioblastoma.

15. The method of claim 6, wherein the tumor is selected from mesothelioma, pancreatic cancer, ovarian cancer, triple negative breast cancer, non-small cell lung cancer, prostate cancer and glioblastoma.

\* \* \* \* \*

SEQUENCE LISTING

```
<160> NUMBER OF SEQ ID NOS: 16

<210> SEQ ID NO 1
<211> LENGTH: 1184
<212> TYPE: DNA
<213> ORGANISM: Artificial Sequence
<220> FEATURE:
<223> OTHER INFORMATION: Chemically Synthesized

<400> SEQUENCE: 1
cgtgaggctc cggtgcccgt cagtgggcag agcgcacatc gcccacagtc cccgagaagt      60
tggggggagg ggtcggcaat tgaaccggtg cctagagaag gtgcgcggg gtaaactggg     120 aaagtgatgt cgtgtactgg ctccgccttt ttcccgaggg tgggggagaa ccgtatataa     180
gtgcagtagt cgccgtgaac gttcttttc gcaacgggtt tgccgccaga acacaggtaa     240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagccccttc gcctcgtgct tgagttgagg     420
cctggcctgg gcgctgggc cgccgcgtgc gaatctggtg gcaccttcgc gcctgtctcg     480
ctgctttcga taagtctcta gccatttaaa attttgatg acctgctgcg acgcttttt      540 tctggcaaga tagtcttgta aatgcgggcc aagatctgca cactggtatt tcggtttttg     600
gggccgcggg cggcgacggg gcccgtgcgt cccagcgcac atgttcggcg aggcggggcc     660
tgcgagcgcg gccaccgaga atcggacggg ggtagtctca agctggccgg cctgctctgg     720
tgcctggcct cgcgccgccg tgtatcgccc cgccctgggc ggcaaggctg gcccggtcgg     780
caccagttgc gtgagcggaa agatggccgc ttcccgccc tgctgcaggg agctcaaaat     840
ggaggacgcg gcgctcggga gagcgggcgg gtgagtcacc cacacaaagg aaaagggcct     900
ttccgtcctc agccgtcgct tcatgtgact ccacggagta ccgggcgccg tccaggcacc     960
tcgattagtt ctcgagcttt tggagtacgt cgtctttagg ttgggggag gggttttatg    1020 cgatggagtt tcccccacact gagtgggtgg agactgaagt taggccagct tggcacttga   1080
tgtaattctc cttggaattt gccctttttg agtttggatc ttggttcatt ctcaagcctc    1140
agacagtggt tcaaagtttt tttcttccat ttcaggtgtc gtga                    1184

<210> SEQ ID NO 2
<211> LENGTH: 63
<212> TYPE: DNA
<213> ORGANISM: Artificial Sequence
<220> FEATURE:
<223> OTHER INFORMATION: Chemically Synthesized

<400> SEQUENCE: 2
atggccttac cagtgaccgc cttgctcctg ccgctggcct tgctgctcca cgccgccagg      60
ccg                                                                   63

<210> SEQ ID NO 3
<211> LENGTH: 720
<212> TYPE: DNA
<213> ORGANISM: Artificial Sequence
<220> FEATURE:
<223> OTHER INFORMATION: Chemically Synthesized
```

<400> SEQUENCE: 3

```
caggtacaac tgcagcagtc tgggcctgag ctggagaagc ctggcgcttc agtgaagata    60
tcctgcaagg cttctggtta ctcattcact ggctacacca tgaactgggt gaagcagagc   120
catgaaaga gccttgagtg gattggactt attactcctt acaatggtgc ttctagctac   180
aaccagaagt tcaggggcaa ggccacatta actgtagaca agtcatccag cacagcctac   240
atggacctcc tcagtctgac atctgaagac tctgcagtct atttctgtgc aaggggggt   300
tacgacggga ggggttttga ctactggggc caagggacca cggtcaccgt ctcctcaggt   360
ggaggcggtt caggcggcgg tggctctagc ggtggcggat cggacatcga gctcactcag   420
tctccagcaa tcatgtctgc atctccaggg gagaaggtca ccatgacctg cagtgccagc   480
tcaagtgtaa gttacatgca ctggtaccag cagaagtcag gcacctcccc caaaagatgg   540
atttatgaca catccaaact ggcttctgga gtcccaggtc gcttcagtgg cagtgggtct   600
ggaaactctt actctctcac aatcagcagc gtggaggctg aagatgatgc aacttattac   660
tgccagcagt ggagtaagca ccctctcacg tacggtgctg gacaaagtt ggaaatcaaa   720
```

<210> SEQ ID NO 4
<211> LENGTH: 135
<212> TYPE: DNA
<213> ORGANISM: Artificial Sequence
<220> FEATURE:
<223> OTHER INFORMATION: Chemically Synthesized

<400> SEQUENCE: 4

```
accacgacgc cagcgccgcg accaccaaca ccggcgccca ccatcgcgtc gcagcccctg    60
tccctgcgcc cagaggcgtg ccggccagcg gcgggggggcg cagtgcacac gaggggctg   120
gacttcgcct gtgat                                                    135
```

<210> SEQ ID NO 5
<211> LENGTH: 72
<212> TYPE: DNA
<213> ORGANISM: Artificial Sequence
<220> FEATURE:
<223> OTHER INFORMATION: Chemically Synthesized

<400> SEQUENCE: 5

```
ttctggttac ccataggatg tgcagccttt gttgtagtct gcattttggg atgcatactt    60
atttgttggc tt                                                       72
```

<210> SEQ ID NO 6
<211> LENGTH: 105
<212> TYPE: DNA
<213> ORGANISM: Artificial Sequence
<220> FEATURE:
<223> OTHER INFORMATION: Chemically Synthesized

<400> SEQUENCE: 6

```
acaaaaaaga agtattcatc cagtgtgcac gaccctaacg gtgaatacat gttcatgaga    60
gcagtgaaca cagccaaaaa atccagactc acagatgtga cccta                  105
```

<210> SEQ ID NO 7
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 7

```
agagtgaagt tcagcaggag cgcagacgcc cccgcgtaca agcagggcca gaaccagctc     60
tataacgagc tcaatctagg acgaagagag gagtacgatg tttggacaa gagacgtggc    120
cgggaccctg agatggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggccttac cagggtctca gtacagccac caaggacacc    300
tacgacgccc ttcacatgca ggccctgccc cctcgc                              336
```

<210> SEQ ID NO 8
<211> LENGTH: 1455
<212> TYPE: DNA
<213> ORGANISM: Artificial Sequence
<220> FEATURE:
<223> OTHER INFORMATION: Chemically Synthesized

<400> SEQUENCE: 8

```
atggccttac cagtgaccgc cttgctcctg ccgctggcct tgctgctcca cgccgccagg     60
ccgggatccc aggtacaact gcagcagtct gggcctgagc tggagaagcc tggcgcttca    120
gtgaagatat cctgcaaggc ttctggttac tcattcactg ctacaccat gaactgggtg    180
aagcagagcc atggaaagag ccttgagtgg attggactta ttactccta caatggtgct    240
tctagctaca accagaagtt caggggcaag gccacattaa ctgtagacaa gtcatccagc    300
acagcctaca tggacctcct cagtctgaca tctgaagact ctgcagtcta tttctgtgca    360
agggggggtt acgacgggag gggttttgac tactgggcc aaggggacac ggtcaccgtc    420
tcctcaggtg gaggcggttc aggcggcggt ggctctagcg gtggcggatc ggacatcgag    480
ctcactcagt ctccagcaat catgtctgca tctccagggg agaaggtcac catgacctgc    540
agtgccagct caagtgtaag ttacatgcac tggtaccagc agaagtcagg cacctccccc    600
aaaagatgga tttatgacac atccaaactg gcttctggag tcccaggtcg cttcagtggc    660
agtgggtctg gaaactctta ctctctcaca atcagcagcg tggaggctga agatgatgca    720
acttattact gccagcagtg gagtaagcac cctctcacgt acggtgctgg gacaaagttg    780
gaaatcaaag ctagcaccac gacgccagcg ccgcgaccac caacaccggc gcccaccatc    840
gcgtcgcagc ccctgtccct gcgcccagag gcgtgccggc cagcggcggg gggcgcagtg    900
cacacgaggg ggctggactt cgcctgtgat ttcgaattct ggttacccat aggatgtgca    960
gcctttgttg tagtctgcat tttgggatgc atacttattt gttggcttac aaaaaagaag   1020
tattcatcca gtgtgcacga ccctaacggt gaatacatgt tcatgagagc agtgaacaca   1080
gccaaaaaat ccagactcac agatgtgacc ctaactagta gagtgaagtt cagcaggagc   1140
gcagacgccc ccgcgtacaa gcagggccag aaccagctct ataacgagct caatctagga   1200
cgaagagagt agtacgatgt tttggacaag agacgtggcc gggaccctga gatgggggga   1260
aagccgagaa ggaagaaccc tcaggaaggc ctgtacaatg aactgcagaa agataagatg   1320
gcggaggcct acagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgc                                                     1455
```

<210> SEQ ID NO 9
<211> LENGTH: 21
<212> TYPE: PRT
<213> ORGANISM: Artificial Sequence

```
<220> FEATURE:
<223> OTHER INFORMATION: Chemically Synthesized

<400> SEQUENCE: 9

Met Ala Leu Pro Val Thr Ala Leu Leu Leu Pro Leu Ala Leu Leu Leu
1               5                   10                  15

His Ala Ala Arg Pro
            20

<210> SEQ ID NO 10
<211> LENGTH: 240
<212> TYPE: PRT
<213> ORGANISM: Artificial Sequence
<220> FEATURE:
<223> OTHER INFORMATION: Chemically Synthesized

<400> SEQUENCE: 10

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser Gly Gly Gly Ser Gly Gly Gly Gly
        115                 120                 125

Ser Ser Gly Gly Gly Ser Asp Ile Glu Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Gly Arg Phe Ser Gly Ser Gly Ser Gly Asn Ser Tyr Ser Leu Thr Ile
        195                 200                 205

Ser Ser Val Glu Ala Glu Asp Asp Ala Thr Tyr Tyr Cys Gln Gln Trp
    210                 215                 220

Ser Lys His Pro Leu Thr Tyr Gly Ala Gly Thr Lys Leu Glu Ile Lys
225                 230                 235                 240

<210> SEQ ID NO 11
<211> LENGTH: 45
<212> TYPE: PRT
<213> ORGANISM: Artificial Sequence
<220> FEATURE:
<223> OTHER INFORMATION: Chemically Synthesized

<400> SEQUENCE: 11

Thr Thr Thr Pro Ala Pro Arg Pro Pro Thr Pro Ala Pro Thr Ile Ala
1               5                   10                  15
```

-continued

```
Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
        35                  40                  45

<210> SEQ ID NO 12
<211> LENGTH: 24
<212> TYPE: PRT
<213> ORGANISM: Artificial Sequence
<220> FEATURE:
<223> OTHER INFORMATION: Chemically Synthesized

<400> SEQUENCE: 12

Phe Trp Leu Pro Ile Gly Cys Ala Ala Phe Val Val Val Cys Ile Leu
1               5                   10                  15

Gly Cys Ile Leu Ile Cys Trp Leu
            20

<210> SEQ ID NO 13
<211> LENGTH: 35
<212> TYPE: PRT
<213> ORGANISM: Artificial Sequence
<220> FEATURE:
<223> OTHER INFORMATION: Chemically Synthesized

<400> SEQUENCE: 13

Thr Lys Lys Lys Tyr Ser Ser Val His Asp Pro Asn Gly Glu Tyr
1               5                   10                  15

Met Phe Met Arg Ala Val Asn Thr Ala Lys Lys Ser Arg Leu Thr Asp
                20                  25                  30

Val Thr Leu
        35

<210> SEQ ID NO 14
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 14

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 15
<211> LENGTH: 485
<212> TYPE: PRT
<213> ORGANISM: Artificial Sequence
<220> FEATURE:
<223> OTHER INFORMATION: Chemically Synthesized
```

<400> SEQUENCE: 15

Met Ala Leu Pro Val Thr Ala Leu Leu Pro Leu Ala Leu Leu Leu
1               5                   10                  15

His Ala Ala Arg Pro Gly Ser Gln Val Gln Leu Gln Gln Ser Gly Pro
                20                  25                  30

Glu Leu Glu Lys Pro Gly Ala Ser Val Lys Ile Ser Cys Lys Ala Ser
            35                  40                  45

Gly Tyr Ser Phe Thr Gly Tyr Thr Met Asn Trp Val Lys Gln Ser His
    50                  55                  60

Gly Lys Ser Leu Glu Trp Ile Gly Leu Ile Thr Pro Tyr Asn Gly Ala
65              70                  75                  80

Ser Ser Tyr Asn Gln Lys Phe Arg Gly Lys Ala Thr Leu Thr Val Asp
                85                  90                  95

Lys Ser Ser Ser Thr Ala Tyr Met Asp Leu Leu Ser Leu Thr Ser Glu
            100                 105                 110

Asp Ser Ala Val Tyr Phe Cys Ala Arg Gly Gly Tyr Asp Gly Arg Gly
        115                 120                 125

Phe Asp Tyr Trp Gly Gln Gly Thr Thr Val Thr Val Ser Ser Gly Gly
    130                 135                 140

Gly Gly Ser Gly Gly Gly Ser Gly Gly Gly Ser Asp Ile Glu
145             150                 155                 160

Leu Thr Gln Ser Pro Ala Ile Met Ser Ala Ser Pro Gly Glu Lys Val
                165                 170                 175

Thr Met Thr Cys Ser Ala Ser Ser Val Ser Tyr Met His Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Gly Arg Phe Ser Gly Ser Gly Ser Gly
    210                 215                 220

Asn Ser Tyr Ser Leu Thr Ile Ser Ser Val Glu Ala Glu Asp Asp Ala
225             230                 235                 240

Thr Tyr Tyr Cys Gln Gln Trp Ser Lys His Pro Leu Thr Tyr Gly Ala
                245                 250                 255

Gly Thr Lys Leu Glu Ile Lys Ala Ser Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Phe Glu Phe Trp Leu Pro Ile Gly Cys Ala
305             310                 315                 320

Ala Phe Val Val Val Cys Ile Leu Gly Cys Ile Leu Ile Cys Trp Leu
                325                 330                 335

Thr Lys Lys Lys Tyr Ser Ser Ser Val His Asp Pro Asn Gly Glu Tyr
            340                 345                 350

Met Phe Met Arg Ala Val Asn Thr Ala Lys Lys Ser Arg Leu Thr Asp
        355                 360                 365

Val Thr Leu Thr Ser Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385             390                 395                 400

Arg Arg Glu Glu Tyr Asp Val Leu Asp Lys Arg Arg Gly Arg Asp Pro

```
                    405                 410                 415
Glu Met Gly Gly Lys Pro Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
            435                 440                 445

Met Lys Gly Glu Arg Arg Gly Lys Gly His Asp Gly Leu Tyr Gln
        450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 16
<211> LENGTH: 2651
<212> TYPE: DNA
<213> ORGANISM: Artificial Sequence
<220> FEATURE:
<223> OTHER INFORMATION: Chemically Synthesized

<400> SEQUENCE: 16
```

| | | | | | |
|---|---|---|---|---|---|
| cgtgaggctc | cggtgcccgt | cagtgggcag | agcgcacatc | gcccacagtc | cccgagaagt | 60 |
| tgggggagg | ggtcggcaat | tgaaccggtg | cctagagaag | gtgcgcgggg | gtaaactggg | 120 |
| aaagtgatgt | cgtgtactgg | ctccgccttt | ttcccgaggg | tggggagaa | ccgtatataa | 180 |
| gtgcagtagt | cgccgtgaac | gttctttttc | gcaacgggtt | tgccgccaga | acacaggtaa | 240 |
| gtgccgtgtg | tggttcccgc | gggcctggcc | tctttacggg | ttatggccct | tgcgtgcctt | 300 |
| gaattacttc | cacctggctg | cagtacgtga | ttcttgatcc | cgagcttcgg | gttggaagtg | 360 |
| ggtgggagag | ttcgaggcct | tgcgcttaag | gagccccttc | gcctcgtgct | tgagttgagg | 420 |
| cctggcctgg | gcgctggggc | cgccgcgtgc | gaatctggtg | gcaccttcgc | gcctgtctcg | 480 |
| ctgctttcga | taagtctcta | gccatttaaa | attttttgatg | acctgctgcg | acgctttttt | 540 |
| tctggcaaga | tagtcttgta | aatgcgggcc | aagatctgca | cactggtatt | tcggttttttg | 600 |
| gggccgcggg | cggcgacggg | gcccgtgcgt | cccagcgcac | atgttcggcg | aggcggggcc | 660 |
| tgcgagcgcg | gccaccgaga | atcggacggg | ggtagtctca | agctggccgg | cctgctctgg | 720 |
| tgcctggcct | cgcgccgccg | tgtatcgccc | cgccctgggc | ggcaaggctg | gcccggtcgg | 780 |
| caccagttgc | gtgagcggaa | agatggccgc | ttcccggccc | tgctgcaggg | agctcaaaat | 840 |
| ggaggacgcg | cgcgctcggga | gagcgggcgg | gtgagtcacc | cacacaaagg | aaaagggcct | 900 |
| ttccgtcctc | agccgtcgct | tcatgtgact | ccacggagta | ccgggcgccg | tccaggcacc | 960 |
| tcgattagtt | ctcgtgcttt | tggagtacgt | cgtctttagg | ttgggggag | gggttttatg | 1020 |
| cgatggagtt | tccccacact | gagtgggtgg | agactgaagt | taggccagct | tggcacttga | 1080 |
| tgtaattctc | cttggaattt | gccctttttg | agtttggatc | ttggttcatt | ctcaagcctc | 1140 |
| agacagtggt | tcaaagtttt | tttcttccat | ttcaggtgtc | gtgagctagc | tctagaatgg | 1200 |
| ccttaccagt | gaccgccttg | ctcctgccgc | tggccttgct | gctccacgcc | gccaggccgg | 1260 |
| gatcccaggt | acaactgcag | cagtctgggc | ctgagctgga | gaagcctggc | gcttcagtga | 1320 |
| agatatcctg | caaggcttct | ggttactcat | tcactggcta | caccatgaac | tgggtgaagc | 1380 |
| agagccatgg | aaagagcctt | gagtggattg | gacttattac | tccttacaat | ggtgcttcta | 1440 |
| gctacaacca | gaagttcagg | ggcaaggcca | cattaactgt | agacaagtca | tccagcacag | 1500 |
| cctacatgga | cctcctcagt | ctgacatctg | aagactctgc | agtctatttc | tgtgcaaggg | 1560 |

```
gggggttacga cgggaggggt tttgactact ggggccaagg gaccacggtc accgtctcct    1620
caggtggagg cggttcaggc ggcggtggct ctagcggtgg cggatcggac atcgagctca    1680
ctcagtctcc agcaatcatg tctgcatctc caggggagaa ggtcaccatg acctgcagtg    1740
ccagctcaag tgtaagttac atgcactggt accagcagaa gtcaggcacc tcccccaaaa    1800
gatggattta tgacacatcc aaactggctt ctggagtccc aggtcgcttc agtggcagtg    1860
ggtctggaaa ctcttactct ctcacaatca gcagcgtgga ggctgaagat gatgcaactt    1920
attactgcca gcagtggagt aagcaccctc tcacgtacgg tgctgggaca aagttggaaa    1980
tcaaagctag caccacgacg ccagcgccgc gaccaccaac accggcgccc accatcgcgt    2040
cgcagcccct gtccctgcgc ccagaggcgt gccggccagc ggcggggggc gcagtgcaca    2100 cgaggggggct ggacttcgcc tgtgatttcg aattctggtt acccatagga tgtgcagcct    2160
ttgttgtagt ctgcattttg ggatgcatac ttatttgttg gcttacaaaa aagaagtatt    2220
catccagtgt gcacgaccct aacggtgaat acatgttcat gagagcagtg aacacagcca    2280
aaaaatccag actcacagat gtgaccctaa ctagtagagt gaagttcagc aggagcgcag    2340
acgcccccgc gtacaagcag ggccagaacc agctctataa cgagctcaat ctaggacgaa    2400
gagaggagta cgatgttttg gacaagagac gtggccggga ccctgagatg gggggaaagc    2460
cgagaaggaa gaaccctcag gaaggcctgt acaatgaact gcagaaagat aagatggcgg    2520
aggcctacag tgagattggg atgaaaggcg agcgccggag gggcaagggg cacgatggcc    2580
tttaccaggg tctcagtaca gccaccaagg acacctacga cgcccttcac atgcaggccc    2640
tgccccctcg c                                                         2651
```